(12) United States Patent
Mansi et al.

(10) Patent No.: US 12,068,070 B2
(45) Date of Patent: Aug. 20, 2024

(54) METHOD AND SYSTEM FOR COMPUTER-AIDED TRIAGE OF STROKE

(71) Applicant: Viz.ai Inc., San Francisco, CA (US)

(72) Inventors: Christopher Mansi, San Francisco, CA (US); David Golan, San Francisco, CA (US); Gil Levi, San Francisco, CA (US); Avraham Wolfson, San Francisco, CA (US); Maayan Goren, San Francisco, CA (US)

(73) Assignee: Viz.ai Inc., San Francisco, CA (US)

( * ) Notice: Subject to any disclaimer, the term of this patent is extended or adjusted under 35 U.S.C. 154(b) by 0 days.

(21) Appl. No.: 17/895,778

(22) Filed: Aug. 25, 2022

(65) Prior Publication Data

US 2022/0415491 A1   Dec. 29, 2022

Related U.S. Application Data

(63) Continuation of application No. 16/913,754, filed on Jun. 26, 2020, now Pat. No. 11,462,318.
(Continued)

(51) Int. Cl.
*G06K 9/00* (2022.01)
*G06N 3/045* (2023.01)
(Continued)

(52) U.S. Cl.
CPC ............ *G16H 40/20* (2018.01); *G06N 3/045* (2023.01); *G06N 3/08* (2013.01);
(Continued)

(58) Field of Classification Search
None
See application file for complete search history.

(56) References Cited

U.S. PATENT DOCUMENTS

| 6,349,330 B1 | 2/2002 | Bernadett et al. |
| 8,374,414 B2 | 2/2013 | Tang et al. |

(Continued)

FOREIGN PATENT DOCUMENTS

| CN | 109003299 A | 12/2018 |
| JP | 2004243117 A | 9/2004 |

(Continued)

OTHER PUBLICATIONS

Cai, Zhaowei, et al., "Cascade R-CNN: High Quality Object Detection and Instance Segmentation", https://arxiv.org/pdf/1906.09756.pdf, Jun. 24, 2019.
(Continued)

*Primary Examiner* — Wei Wen Yang
(74) *Attorney, Agent, or Firm* — Jeffrey Schox

(57) ABSTRACT

A system for computer-aided triage includes a router, a remote computing system, and a client application. Additionally or alternatively, the system 100 can include any number of computing systems, servers, storage, lookup table, memory, and/or any other suitable components. A method for computer-aided triage includes receiving a data packet associated with a patient and taken at a first point of care; checking for a suspected condition associated with the data packet; in an event that the suspected condition is detected, determining a recipient based on the suspected condition; and transmitting information to a device associated with the recipient.

21 Claims, 16 Drawing Sheets

Related U.S. Application Data

(60) Provisional application No. 62/867,566, filed on Jun. 27, 2019.

(51) Int. Cl.
*G06N 3/08* (2023.01)
*G06Q 10/0631* (2023.01)
*G06T 7/00* (2017.01)
*G06T 7/11* (2017.01)
*G06T 7/62* (2017.01)
*G06T 11/00* (2006.01)
*G16H 10/20* (2018.01)
*G16H 15/00* (2018.01)
*G16H 30/40* (2018.01)
*G16H 40/20* (2018.01)
*G16H 50/20* (2018.01)
*G16H 50/30* (2018.01)
*G16H 80/00* (2018.01)

(52) U.S. Cl.
CPC ...... *G06Q 10/06311* (2013.01); *G06T 7/0012* (2013.01); *G06T 7/11* (2017.01); *G06T 7/62* (2017.01); *G06T 11/001* (2013.01); *G16H 10/20* (2018.01); *G16H 15/00* (2018.01); *G16H 30/40* (2018.01); *G16H 50/20* (2018.01); *G16H 50/30* (2018.01); *G16H 80/00* (2018.01); *G06T 2207/20081* (2013.01); *G06T 2207/30016* (2013.01); *G06T 2210/41* (2013.01)

(56) References Cited

U.S. PATENT DOCUMENTS

| | | | |
|---|---|---|---|
| 9,307,918 | B2 | 4/2016 | Kinrot et al. |
| 9,439,622 | B2 | 9/2016 | Case et al. |
| 10,346,979 | B2 | 7/2019 | Mansi et al. |
| 10,373,315 | B2 | 8/2019 | Mansi et al. |
| 10,733,730 | B2 | 8/2020 | Mansi et al. |
| 10,835,257 | B2 | 11/2020 | Ferrera et al. |
| 10,853,449 | B1 | 12/2020 | Nguyen et al. |
| 10,902,602 | B1 | 1/2021 | Mansi et al. |
| 11,241,169 | B2 | 2/2022 | Kusens et al. |
| 11,316,941 | B1 | 4/2022 | Jain et al. |
| 11,328,400 | B2 | 5/2022 | Levi et al. |
| 11,462,318 | B2 | 10/2022 | Mansi et al. |
| 11,521,714 | B1 | 12/2022 | Jain et al. |
| 11,694,807 | B2 | 7/2023 | Golan et al. |
| 2004/0161137 | A1 | 8/2004 | Aben et al. |
| 2006/0140473 | A1 | 6/2006 | Brooksby et al. |
| 2007/0019846 | A1 | 1/2007 | Bullitt et al. |
| 2008/0021502 | A1 | 1/2008 | Imielinska et al. |
| 2009/0028403 | A1 | 1/2009 | Bar-Aviv et al. |
| 2009/0129649 | A1 | 5/2009 | Djeridane |
| 2009/0279752 | A1 | 11/2009 | Sirohey et al. |
| 2010/0106002 | A1 | 4/2010 | Sugiyama et al. |
| 2011/0028825 | A1 | 2/2011 | Douglas et al. |
| 2011/0052024 | A1 | 3/2011 | Nowinski |
| 2011/0116702 | A1 | 5/2011 | Bredno et al. |
| 2011/0172550 | A1 | 7/2011 | Martin et al. |
| 2012/0065987 | A1 | 3/2012 | Farooq et al. |
| 2012/0201446 | A1 | 8/2012 | Yang et al. |
| 2012/0237103 | A1 | 9/2012 | Hu |
| 2013/0185096 | A1 | 7/2013 | Giusti et al. |
| 2013/0208955 | A1 | 8/2013 | Zhao et al. |
| 2013/0208966 | A1 | 8/2013 | Zhao et al. |
| 2014/0142982 | A1 | 5/2014 | Janssens |
| 2014/0142983 | A1 | 5/2014 | Backhaus et al. |
| 2014/0222444 | A1 | 8/2014 | Cerello et al. |
| 2014/0257854 | A1 | 9/2014 | Becker et al. |
| 2014/0348408 | A1 | 11/2014 | Zhu et al. |
| 2015/0011902 | A1 | 1/2015 | Wang |
| 2015/0104102 | A1 | 4/2015 | Carreira et al. |
| 2015/0208994 | A1 | 7/2015 | Rapoport |
| 2015/0320365 | A1 | 11/2015 | Schulze et al. |
| 2016/0037057 | A1 | 2/2016 | Westin et al. |
| 2016/0063191 | A1 | 3/2016 | Vesto et al. |
| 2016/0100302 | A1 | 4/2016 | Barash et al. |
| 2016/0110890 | A1 | 4/2016 | Smith |
| 2016/0135706 | A1 | 5/2016 | Sullivan et al. |
| 2016/0180042 | A1 | 6/2016 | Menon et al. |
| 2016/0188829 | A1 | 6/2016 | Southerland et al. |
| 2017/0007167 | A1 | 1/2017 | Kostic et al. |
| 2017/0143428 | A1 | 5/2017 | Raffy et al. |
| 2017/0147765 | A1 | 5/2017 | Mehta |
| 2017/0181657 | A1 | 6/2017 | Jin et al. |
| 2017/0228501 | A1 | 8/2017 | Turner et al. |
| 2017/0228516 | A1 | 8/2017 | Sampath et al. |
| 2017/0258433 | A1 | 9/2017 | Gulsun et al. |
| 2017/0300654 | A1 | 10/2017 | Stein et al. |
| 2017/0340260 | A1 | 11/2017 | Chowdhury et al. |
| 2018/0025255 | A1 | 1/2018 | Poole et al. |
| 2018/0085001 | A1 | 3/2018 | Berger et al. |
| 2018/0110475 | A1 | 4/2018 | Shaya |
| 2018/0116620 | A1 | 5/2018 | Chen et al. |
| 2018/0235482 | A1 | 8/2018 | Fonte et al. |
| 2018/0253530 | A1 | 9/2018 | Goldberg et al. |
| 2018/0365824 | A1 | 12/2018 | Yuh et al. |
| 2018/0365828 | A1 | 12/2018 | Mansi et al. |
| 2018/0366225 | A1 | 12/2018 | Mansi et al. |
| 2019/0130228 | A1* | 5/2019 | Fu .................. G06N 5/01 |
| 2019/0156937 | A1 | 5/2019 | Shimomura et al. |
| 2019/0380643 | A1 | 12/2019 | Kochura et al. |
| 2020/0058410 | A1 | 2/2020 | Khouri et al. |
| 2020/0090331 | A1 | 3/2020 | Mansi et al. |
| 2020/0294241 | A1 | 9/2020 | Wu et al. |
| 2021/0057112 | A1 | 2/2021 | Mansi et al. |
| 2021/0137384 | A1 | 5/2021 | Robinson et al. |
| 2021/0334958 | A1 | 10/2021 | Siow et al. |
| 2022/0028524 | A1 | 1/2022 | Levi et al. |
| 2022/0087631 | A1 | 3/2022 | D'Esterre et al. |

FOREIGN PATENT DOCUMENTS

| | | |
|---|---|---|
| JP | 4854717 B2 | 11/2011 |
| JP | 2012027565 A | 2/2012 |
| WO | 2016134125 A1 | 8/2016 |

OTHER PUBLICATIONS

Gupta, Akshat , et al., "Delineation of Ischemic Core and Penumbra Volumes from MRI using MSNet Architecture", Annu Int Conf IEEE Eng Med Biol Soc. Jul. 2019;2019:6730-6733.

He, Kaiming , et al., "Mask R-CNN", https://arxiv.org/pdf/1703.06870.pdf, Jan. 24, 2018.

Ker, Justin , et al., "Image Thresholding Improves 3-Dimensional Convolutional Neural Network 1-21 Diagnosis of Different Acute Brain Hemorrhages on Computed Tomography Scans", Sensors 2019, 2167,May 10, 2019, www.mdpi.com.com/journal/sensors.

Keshavamurthy, K. , et al., "Machine learning algorithm for automatic detection of CT-identifiable hyperdense lesions associated with traumatic brain injury", Mar. 23, 2017, SPIE Medical Imaging, Orlando, Florida.

Kirisil, H.A. , et al., "Standardized evaluation framework for evaluating coronary artery stenosis detection, stenosis quantification and lumen segmentation algorithms in computed tomography angiography", Elsevier, 2013, pp. 859-876.

Kuang, Hulin , et al., "Segmenting Hemorrhagic and Ischemic Infarct Simultaneously From Follow-Up Non-Contrast CT Images in Patients With Acute Ischemic Stroke", IEEE Access, vol. 7, May 22, 2019.

Lewis, Thomas L., et al., "Ambulance smartphone tool for field triage of ruptured aortic aneurysms (FILTR): study protocol for a prospective observational validation of diagnostic accuracy", BMJ Open 2016, pp. 1-5 , https://bmjopen.bmj.com/content/bmjopen/6/10/e011308.full.pdf.

Lidayova, Kristina , et al., "Skeleton-based 1-3,6-15 fast, fully automated generation of vessel tree structure for clinical evaluation of blood vessel systems", In: Skeletonization : theory, methods and applications, Jun. 1, 2017.

(56) References Cited

OTHER PUBLICATIONS

Liu, Liyuan, et al., "On the Variance of the Adaptive Learning Rate and Beyond", https://arxiv.org/pdf/1908.03265.pdf, Apr. 17, 2020, Published as a conference paper at ICLR 2020.

Madhuripan, Nikhil, et al., "Computed Tomography Angiography in Head and Neck Emergencies", Seminars in Ultrasound and CT and MRI, US, vol. 38, No. 4, 2017. Feb. 20, 2017 (Feb. 20, 2017), pp. 345-356.

Mittal, Sushil, et al., "Fast Automatic Detection of Calcified Coronary Lesions in 3D Cardiac CT Images", MLMI 2010, pp. 1-9.

Smith, Wade S., et al., "Prognostic Significance of Angiographically Confirmed Large Vessel Intracranial Occlusion in Patients Presenting With Acute Brain Ischemia", Neurocritical Care, vol. 4, 2006.

Yu, Y., et al., "Use of Deep Learning to Predict Final Ischemic Stroke Lesions From Initial Magnetic Resonance Imaging", Mar. 1, 2020, https://europepmc.org/article/med/32163165.

Zerna, C., et al., "Imaging, Intervention, and Workflow in Acute Ischemic Strike: The Calgary Approach", AJNR M J Neuroradiol 37.978-84, Jun. 2016, pp. 978-984.

Keshavamurthy, Krishna, "Machine learning algorithm for automatic detection of CT-identifiable hyperdense lesions associated with traumatic brain injury", Proc. of SPIE vol. 10134 2017.

\* cited by examiner

User device (e.g., of research coordinator of clinical trial)

5:04

Urgent: ICH suspected
69F @ St. Hill Hospital

A.I. has identified an ICH with a volume of 14 cc for your immediate review

Notification

FIGURE 12

METHOD AND SYSTEM FOR COMPUTER-AIDED TRIAGE OF STROKE

CROSS-REFERENCE TO RELATED APPLICATIONS

This application is continuation of U.S. application Ser. No. 16/913,754, filed 26 Jun. 2020, which claims the benefit of U.S. Provisional Application No. 62/867,566, filed 27 Jun. 2019, each of which is incorporated herein in its entirety by this reference.

TECHNICAL FIELD

This invention relates generally to the medical diagnostic field, and more specifically to a new and useful system and method for computer-aided triage in the medical diagnostic field.

BACKGROUND

In current triaging workflows, especially those in an emergency setting, a patient presents at a first point of care, where an assessment, such as imaging, is performed. The image data is then sent to a standard radiology workflow, which typically involves: images being uploaded to a radiologist's queue, the radiologist reviewing the images at a workstation, the radiologist generating a report, an emergency department doctor reviewing the radiologist's report, the emergency department doctor determining and contact a specialist, and making a decision of how to treat and/or transfer the patient to a $2^{nd}$ point of care. This workflow is typically very time-consuming, which increases the time it takes to treat and/or transfer a patient to a specialist. In many conditions, especially those involving stroke, time is extremely sensitive, as it is estimated that in the case of stroke, a patient loses about 1.9 million neurons per minute that the stroke is left untreated (Saver et al.). Further, as time passes, the amount and types of treatment options available to the patient decrease.

Thus, there is a need in the triaging field to create an improved and useful system and method for decreasing the time it takes to determine and initiate treatment for a patient presenting with a critical condition.

BRIEF DESCRIPTION OF THE FIGURES

FIG. 12 depicts a variation of a notification transmitted to a device of a participant.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Overview

Figure 1:
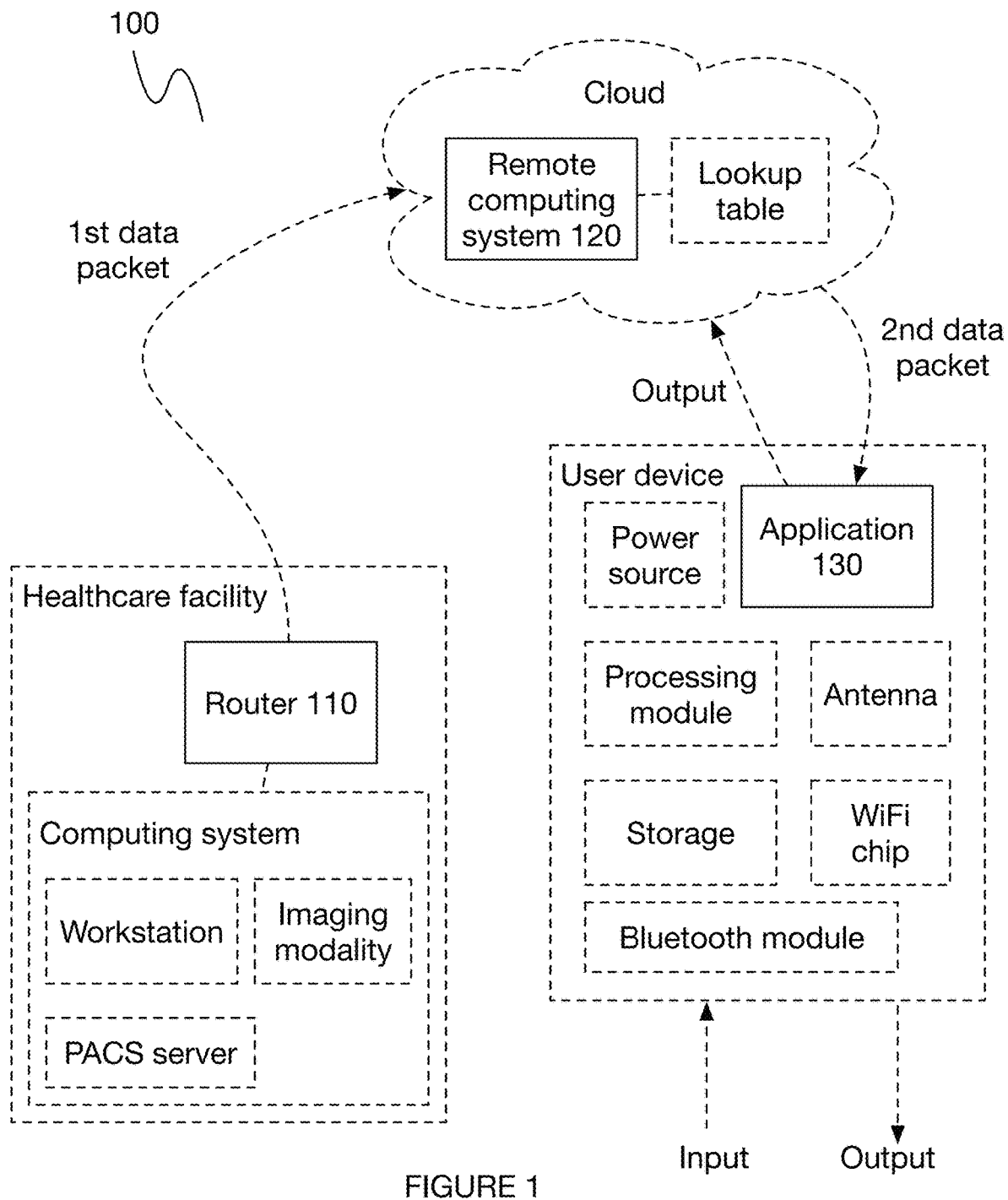
FIG. 1 is a schematic of a system for computer-aided triage.

As shown in FIG. 1, a system 100 for computer-aided triage includes a router, a remote computing system, and a client application. Additionally or alternatively, the system 100 can include any number of computing systems (e.g., local, remote), servers (e.g., PACS server), storage, lookup table, memory, and/or any other suitable components. Further additionally or alternatively, the system can include any or all of the components, embodiments, and examples as described in any or all of: U.S. application Ser. No. 16/012,458, filed 19 Jun. 2018; U.S. application Ser. No. 16/012,495, filed 19 Jun. 2018; and U.S. application Ser. No. 16/688,721, filed 19 Nov. 2019, each of which is incorporated in its entirety by this reference.

Figure 2:
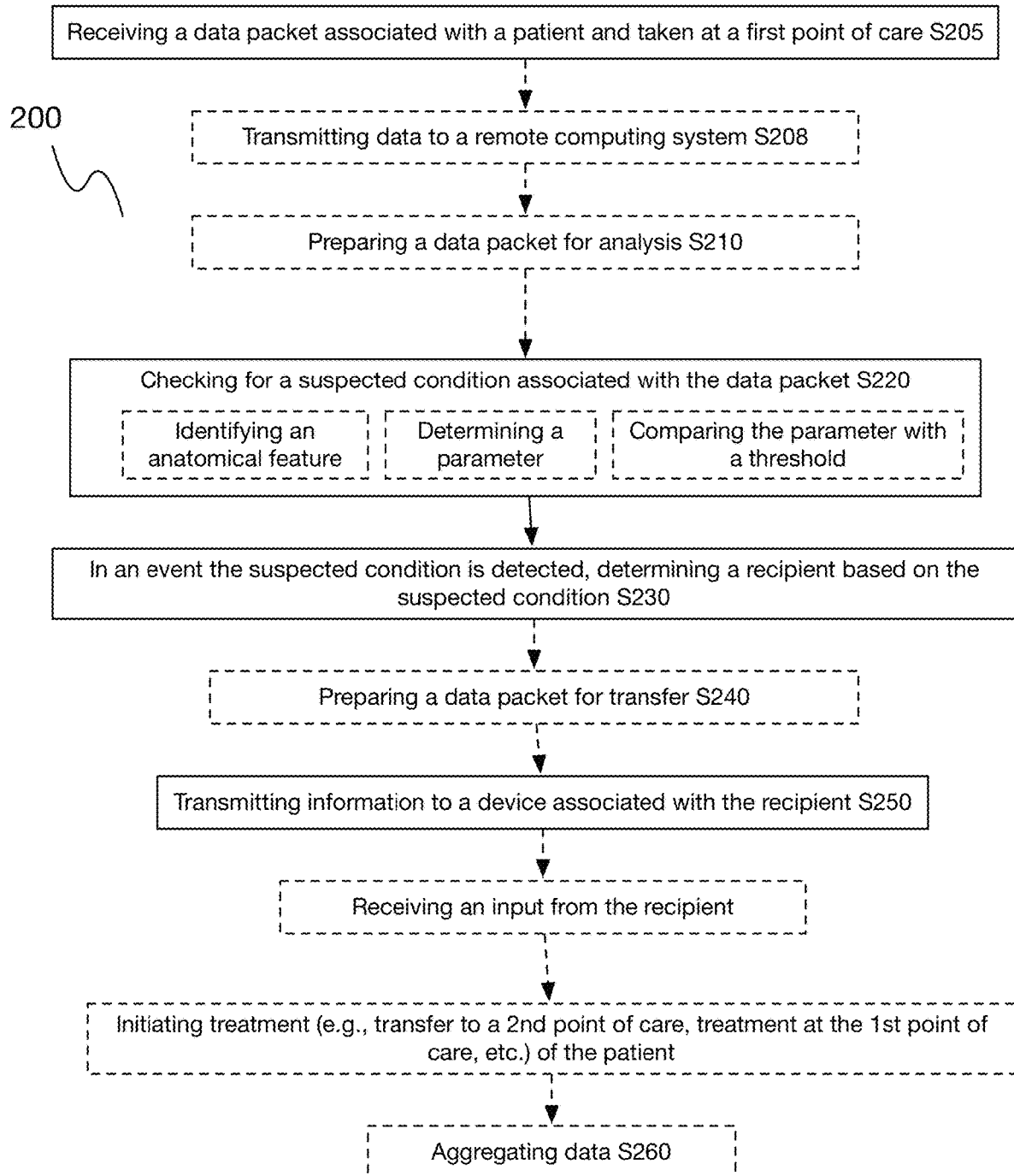
FIG. 2 is a schematic of a method for computer-aided triage.

As shown in FIG. 2, a method 200 for computer-aided triage includes receiving a data packet associated with a patient and taken at a first point of care S205; checking for a suspected condition associated with the data packet S220; in an event that the suspected condition is detected, determining a recipient based on the suspected condition S230; and transmitting information to a device associated with the recipient S250. Additionally or alternatively, the method 200 can include any or all of: transmitting data to a remote computing system S208; preparing a data packet for analysis S210; determining a parameter associated with a data packet; determining a treatment option based on the parameter; preparing a data packet for transfer S240; receiving an input from the recipient; initiating treatment of the patient; transmitting information to a device associated with a second point of care S150; and/or any other suitable processes. Further additionally or alternatively, the method 200 can include any or all of the processes, embodiments, and examples described in any or all of: U.S. application Ser. No. 16/012,458, filed 19 Jun. 2018; U.S. application Ser. No. 16/012,495, filed 19 Jun. 2018; and U.S. application Ser. No. 16/688,721, filed 19 Nov. 2019, each of which is incorporated in its entirety by this reference, or any other suitable processes performed in any suitable order. The method 200 can be performed with a system as described above and/or any other suitable system.

2. Benefits

The system and method for computer-aided triage can confer several benefits over current systems and methods.

In a first variation, the system and/or method confer the benefit of reducing the time to match and/or transfer a patient presenting with a condition (e.g., hemorrhage, intracerebral hemorrhage [ICH]) to a specialist. In a specific example, for instance, the average time between generating a non-contrast dataset and notifying a specialist (e.g., in a case associated with a suspected condition) is reduced from over 30 minutes (e.g., 35 minutes, 40 minutes, 45 minutes, 50 minutes, greater than 50 minutes, etc.) to less than 8 minutes (e.g., 30 seconds, less than a minute, between 1-2 minutes, 2 minutes, between 2-3 minutes, 3 minutes, between 3-4 minutes, etc.).

In a second variation, the system and/or method provide a parallel process to a traditional workflow (e.g., standard radiology workflow), which can confer the benefit of reducing the time to determine a treatment option while having the outcome of the traditional workflow as a backup in the case that an inconclusive or inaccurate determination (e.g., false negative, false positive, etc.) results from the method. Additionally or alternatively, the system and/or method can be implemented in place of and/or integrated within a traditional workflow (e.g., the standard radiology workflow).

In a third variation, the system and/or method is configured to have a high sensitivity (e.g., 87.8%, approximately 88%, between 81% and 93%, greater than 87%, etc.), which functions to detect a high number of true positive cases and help these patients reach treatment faster. In the event that this results in a false positive, only a minor disturbance—if any—is caused to a specialist, which affects the specialist's workflow negligibly (e.g., less than 5 minutes), if at all. In a specific example, the method is configured to have a sensitivity above a predetermined threshold after a particular category of artifacts (e.g., motion artifacts, metal artifacts, etc.) have been checked for.

In a fourth variation, the system and/or method confer the benefit of minimizing the occurrence of false positive cases (e.g., less than 10% occurrence, less than 5% occurrence, less than, which functions to minimize disturbances caused to specialists or other individuals. This can function to minimize unnecessary disturbances to specialists in variations in which specialists or other users are notified on a mobile device upon detection of a potential brain condition (e.g., ICH), as it can minimize the occurrence of a specialist being alerted (e.g., potentially at inconvenient times of day, while the specialist is otherwise occupied, etc.) for false positives, while still maintaining a fallback in the standard radiology workflow in the event that a true positive is missed. In a set of specific examples, the method includes training (e.g., iteratively training) a set of deep learning models involved in ICH detection on images originally detected to be a true positive but later identified as a false positive.

In a fifth variation, the system and/or method confer the benefit of reorganizing a queue of patients, wherein patients having a certain condition are detected early and prioritized (e.g., moved to the front of the queue).

In a sixth variation, the system and/or method confer the benefit of determining actionable analytics to optimize a workflow, such as an emergency room triage workflow.

In a seventh variation, the system and/or method confer the benefit of automatically determining a potential hemorrhage (e.g., ICH) in a set of non-contrast scans and notifying a specialist prior to the identification of a potential ICH by a radiologist during a parallel workflow.

In an eighth variation, the system and/or method confer the benefit of recommending a patient for a clinical trial based on an automated processing of a set of images (e.g., brain images) associated with the patient.

In a ninth variation, the system and/or method confer the benefit of determining a suspected patient condition with a sensitivity of at least 95% (e.g., 96%, 97%, between 96% and 97%, etc.) and a specificity of at least 94% (e.g., 96%, 97%, between 96% and 97%, etc.).

Additionally or alternatively, the system and method can confer any other benefit.

3. System

The system preferably interfaces with one or more points of care (e.g., $1^{st}$ point of care, $2^{nd}$ point of care, $3^{rd}$ point of care, etc.), each of which are typically a healthcare facility. A $1^{st}$ point of care herein refers to the healthcare facility at which a patient presents, typically where the patient first presents (e.g., in an emergency setting). Conventionally, healthcare facilities include spoke facilities, which are often general (e.g., non-specialist, emergency, etc.) facilities, and hub (e.g., specialist) facilities, which can be equipped or better equipped (e.g., in comparison to spoke facilities) for certain procedures (e.g., mechanical thrombectomy), conditions (e.g., stroke), or patients (e.g., high risk). Patients typically present to a spoke facility at a $1^{st}$ point of care, but can alternatively present to a hub facility, such as when it is evident what condition their symptoms reflect, when they have a prior history of a serious condition, when the condition has progressed to a high severity, when a hub facility is closest, randomly, or for any other reason. A healthcare facility can include any or all of: a hospital, clinic, ambulances, doctor's office, imaging center, laboratory, primary stroke center (PSC), comprehensive stroke center (CSC), stroke ready center, interventional ready center, or any other suitable facility involved in patient care and/or diagnostic testing.

A patient can be presenting with symptoms of a condition, no symptoms (e.g., presenting for routine testing), or for any other suitable system. In some variations, the patient is presenting with one or more stroke symptoms (e.g., hemorrhagic stroke symptoms), such as, but not limited to: weakness, numbness, speech abnormalities, and facial drooping. Typically, these patients are then treated in accordance with a stroke protocol, which typically involves an imaging protocol at an imaging modality, such as, but not limited to: a non-contrast CT (NCCT) scan of the head, a CTA scan of the head and neck, a CT perfusion (CTP) scan of the head.

A healthcare worker herein refers to any individual or entity associated with a healthcare facility, such as, but not limited to: a physician, emergency room physician (e.g., orders appropriate lab and imaging tests in accordance with a stroke protocol), radiologist (e.g., on-duty radiologist, healthcare worker reviewing a completed imaging study, healthcare working authoring a final report, etc.), neuroradiologist, specialist (e.g., neurovascular specialist, vascular neurologist, neuro-interventional specialist, neuro-endovascular specialist, expert/specialist in a procedure such as mechanical thrombectomy, cardiac specialist, etc.), administrative assistant, healthcare facility employee (e.g., staff employee), emergency responder (e.g., emergency medical technician), or any other suitable individual.

The image data can include computed tomography (CT) data (e.g., radiographic CT, non-contrast CT, CT perfusion, etc.), preferably non-contrast CT data (e.g., axial data, axial series of slices, consecutive slices, etc.) but can additionally or alternatively any other suitable image data. The image data is preferably generated at an imaging modality (e.g., scanner at the $1^{st}$ point of care), such as a CT scanner, magnetic resonance imaging (MRI) scanner, ultrasound system, or any other scanner. Additionally or alternatively, image data can be generated from a camera, user device, accessed from a database or web-based platform, drawn, sketched, or otherwise obtained.

3.1 System—Router 110

The system 100 can include a router no (e.g., medical routing system), which functions to receive a data packet (e.g., dataset) including instances (e.g., images, scans, etc.) taken at an imaging modality (e.g., scanner) via a computing system (e.g., scanner, workstation, PACS server) associated with a $1^{st}$ point of care. The instances are preferably in the Digital Imaging and Communications in Medicine (DICOM) file format, as well as generated and transferred between computing system in accordance with a DICOM protocol, but can additionally or alternatively be in any suitable format. Additionally or alternatively, the instances can include any suitable medical data (e.g., diagnostic data, patient data, patient history, patient demographic information, etc.), such as, but not limited to, PACS data, Health-Level 7 (HL7) data, electronic health record (EHR) data, or any other suitable data, and to forward the data to a remote computing system.

The instances preferably include (e.g., are tagged with) and/or associated with a set of metadata, but can additionally or alternatively include multiple sets of metadata, no metadata, extracted (e.g., removed) metadata (e.g., for regulatory purposes, HIPAA compliance, etc.), altered (e.g., encrypted, decrypted, deidentified, anonymized etc.) metadata, or any other suitable metadata, tags, identifiers, or other suitable information.

The router 110 can refer to or include a virtual entity (e.g., virtual machine, virtual server, etc.) and/or a physical entity (e.g., local server). The router can be local (e.g., at a $1^{st}$ healthcare facility, $2^{nd}$ healthcare facility, etc.) and associated with (e.g., connected to) any or all of: on-site server associated with any or all of the imaging modality, the healthcare facility's PACS architecture (e.g., server associated with physician workstations), or any other suitable local server or DICOM compatible device(s). Additionally or alternatively, the router can be remote (e.g., locate at a remote facility, remote server, cloud computing system, etc.), and associated with any or all of: a remote server associated with the PACS system, a modality, or another DICOM compatible device such as a DICOM router.

The router 110 preferably operates on (e.g., is integrated into) a system (e.g., computing system, workstation, server, PACS server, imaging modality, scanner, etc.) at a $1^{st}$ point of care but additionally or alternatively, at a $2^{nd}$ point of care, remote server (e.g., physical, virtual, etc.) associated with one or both of the $1^{st}$ point of care and the $2^{nd}$ point of care (e.g., PACS server, EHR server, HL7 server), a data storage system (e.g., patient records), or any other suitable system. In some variations, the system that the router operates on is physical (e.g., physical workstation, imaging modality, scanner, etc.) but can additionally or alternatively include virtual components (e.g., virtual server, virtual database, cloud computing system, etc.).

The router 110 is preferably configured to receive data (e.g., instances, images, study, series, etc.) from an imaging modality, preferably an imaging modality (e.g., CT scanner, MRI scanner, ultrasound machine, etc.) at a first point of care (e.g., spoke, hub, etc.) but can additionally or alternatively be at a second point of care (e.g., hub, spoke, etc.), multiple points of care, or any other healthcare facility. The router can be coupled in any suitable way (e.g., wired connection, wireless connection, etc.) to the imaging modality (e.g., directly connected, indirectly connected via a PACS server, etc.). Additionally or alternatively, the router can be connected to the healthcare facility's PACS architecture, or other server or DICOM-compatible device of any point of care or healthcare facility.

In some variations, the router includes a virtual machine operating on a computing system (e.g., computer, workstation, user device, etc.), imaging modality (e.g., scanner), server (e.g., PACS server, server at $1^{st}$ healthcare facility, server at $2^{nd}$ healthcare facility, etc.), or other system. In a specific example, the router is part of a virtual machine server. In another specific example, the router is part of a local server.

3.2 System—Remote Computing System 120

The system 100 can include a remote computing system 120, which can function to receive and process data packets (e.g., dataset from router), determine a treatment option (e.g., select a $2^{nd}$ point of care, select a specialist, etc.), interface with a user device (e.g., mobile device), compress a data packet, extract and/or remove metadata from a data packet (e.g., to comply with a regulatory agency), or perform any other suitable function.

Preferably, part of the method 200 is performed at the remote computing system (e.g., cloud-based), but additionally or alternatively all of the method 200 can be performed at the remote computing system, the method 200 can be performed at any other suitable computing system(s). In some variations, the remote computing system 120 provides an interface for technical support (e.g., for a client application) and/or analytics. In some variations, the remote computing system includes storage and is configured to store and/or access a lookup table, wherein the lookup table functions to determine a treatment option (e.g., $2^{nd}$ point of care), a contact associated with the $2^{nd}$ point of care, and/or any other suitable information.

In some variations, the remote computing system 120 connects multiple healthcare facilities (e.g., through a client application, through a messaging platform, etc.).

In some variations, the remote computing system 120 functions to receive one or more inputs and/or to monitor a set of client applications (e.g., executing on user devices, executing on workstations, etc.).

3.3 System—Application 130

Figure 5A:
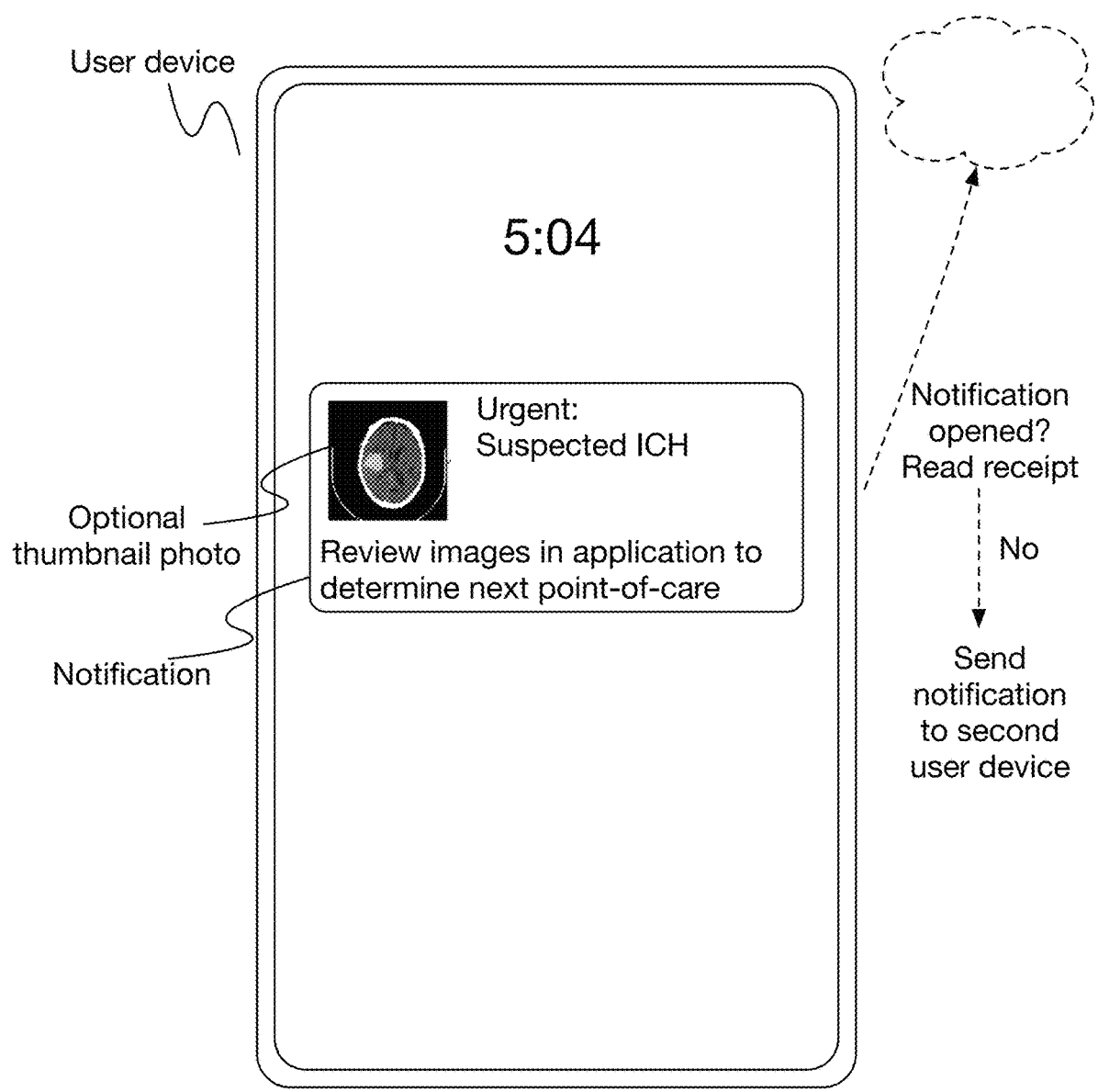
FIGS. 5A and 5B depict a variation of an application on a user device.
Figure 5B:
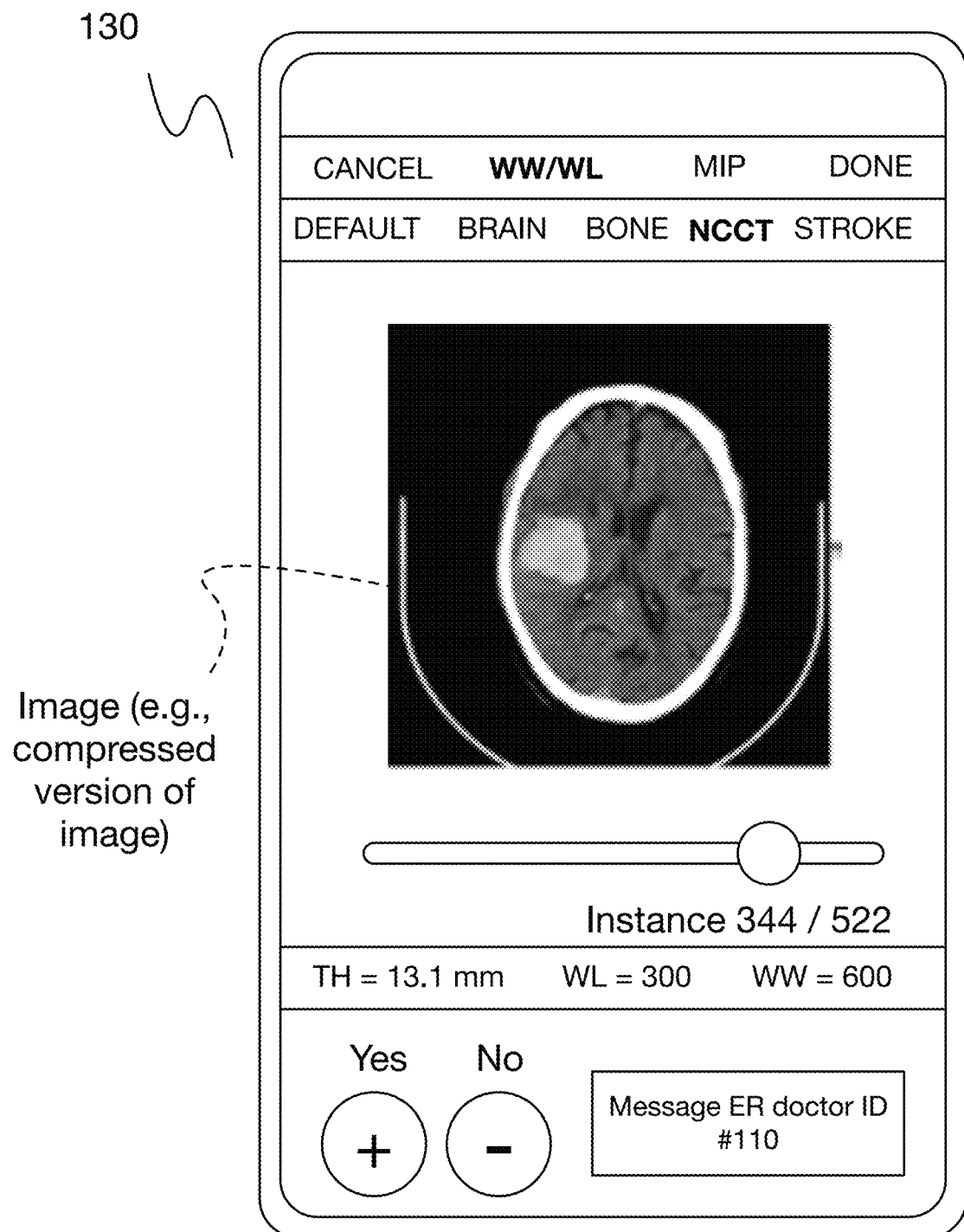

The system 100 can include one or more applications 130 (e.g., clients, client applications, client application executing on a device, etc.), such as the application shown in FIGS. 5A and 5B, which individually or collectively function to provide one or more outputs (e.g., from the remote computing system) to a contact. Additionally or alternatively, the applications can individually or collectively function to receive one or more inputs from a contact, provide one or more outputs to a healthcare facility (e.g., first point of care, second point of care, etc.), establish communication between healthcare facilities, or perform any other suitable function.

In some variations, one or more features of the application (e.g., appearance, information content, information displayed, user interface, graphical user interface, etc.) are determined based on any or all of: the type of device that the application is operating on (e.g., user device vs. healthcare facility device, mobile device vs. stationary device), where the device is located (e.g., $1^{st}$ point of care, $2^{nd}$ point of care, etc.), who is interacting with the application (e.g., user identifier, user security clearance, user permission, etc.), or any other characteristic. In some variations, for instance, an application executing on a healthcare facility will display a $1^{st}$ set of information (e.g., uncompressed images, metadata, etc.) while an application executing on a user device will display a $2^{nd}$ set of information (e.g., compressed images, no metadata, etc.). In some variations, the type of data to display is determined based on any or all of: an application identifier, mobile device identifier, workstation identifier, or any other suitable identifier.

The outputs of the application can include any or all of: an alert or notification (e.g., push notification, text message, call, email, etc.); an image set (e.g., compressed version of images taken at scanner, preview of images taken at scanner, images taken at scanner, etc.); a set of tools for interacting with the image set, such as any or all of panning, zooming, rotating, adjusting window level and width, scrolling, performing maximum intensity projection [MIP] (e.g., option to select the slab thickness of a MIP), changing the orientation of a 3D scan (e.g., changing between axial, coronal, and sagittal views, freestyle orientation change), showing multiple views of a set of images; a worklist (e.g., list of patients presenting for and/or requiring care, patients being taken care of by specialist, patients recommended to specialist, procedures to be performed by specialist, etc.); a messaging platform (e.g., HIPAA-compliant messaging platform, texting platform, video messaging, group messaging etc.); a telecommunication platform (e.g., video conferencing platform); a directory of contact information (e.g., $1^{st}$ point of care contact info, $2^{nd}$ point of care contact info, etc.); tracking of a workflow or activity (e.g., real-time or near real-time updates of patient status/workflow/etc.); analytics based on or related to the tracking (e.g., predictive analytics such as predicted time remaining in radiology workflow or predicted time until stroke reaches a certain severity; average time in a workflow; average time to transition to a second point of care, etc.); or any other suitable output.

The inputs can include any or all of the outputs described previously, touch inputs (e.g., received at a touch-sensitive surface), audio inputs, optical inputs, or any other suitable input. The set of inputs preferably includes an input indicating receipt of an output by a recipient (e.g., read receipt of a specialist upon opening a notification). This can include an active input from the contact (e.g., contact makes selection at application), a passive input (e.g., read receipt), or any other input.

In one variation, the system 100 includes a mobile device application 130 and a workstation application 130—both connected to the remote computing system—wherein a shared user identifier (e.g., specialist account, user account, etc.) can be used to connect the applications (e.g., retrieve a case, image set, etc.) and determine the information to be displayed at each application (e.g., variations of image datasets). In one example, the information to be displayed (e.g., compressed images, high-resolution images, etc.) can be determined based on: the system type (e.g., mobile device, workstation), the application type (e.g., mobile device application, workstation application), the user account (e.g., permissions, etc.), any other suitable information, or otherwise determined.

The application can include any suitable algorithms or processes for analysis, and part or all of the method 200 can be performed by a processor associated with the application.

The application preferably includes both front-end (e.g., application executing on a user device, application executing on a workstation, etc.) and back-end components (e.g., software, processing at a remote computing system, etc.), but can additionally or alternatively include just front-end or back-end components, or any number of components implemented at any suitable system(s).

3.4 System—Additional Components

The system 100 and/or or any component of the system 100 can optionally include or be coupled to any suitable component for operation, such as, but not limited to: a processing module (e.g., processor, microprocessor, etc.), control module (e.g., controller, microcontroller), power module (e.g., power source, battery, rechargeable battery, mains power, inductive charger, etc.), sensor system (e.g., optical sensor, camera, microphone, motion sensor, location sensor, etc.), or any other suitable component.

4. Method

As shown in FIG. 2, the method 200 includes receiving a data packet associated with a patient and taken at a first point of care S205; checking for a suspected condition associated with the data packet S220; in an event that the suspected condition is detected, determining a recipient based on the suspected condition S230; and transmitting information to a device associated with the recipient S250. Additionally or alternatively, the method 200 can include any or all of: transmitting data to a remote computing system S208; preparing a data packet for analysis S210; determining a parameter associated with a data packet; determining a treatment option based on the parameter; preparing a data packet for transfer S240; receiving an input from the recipient; initiating treatment of the patient; transmitting information to a device associated with a second point of care S150; and/or any other suitable processes.

Figure 3:
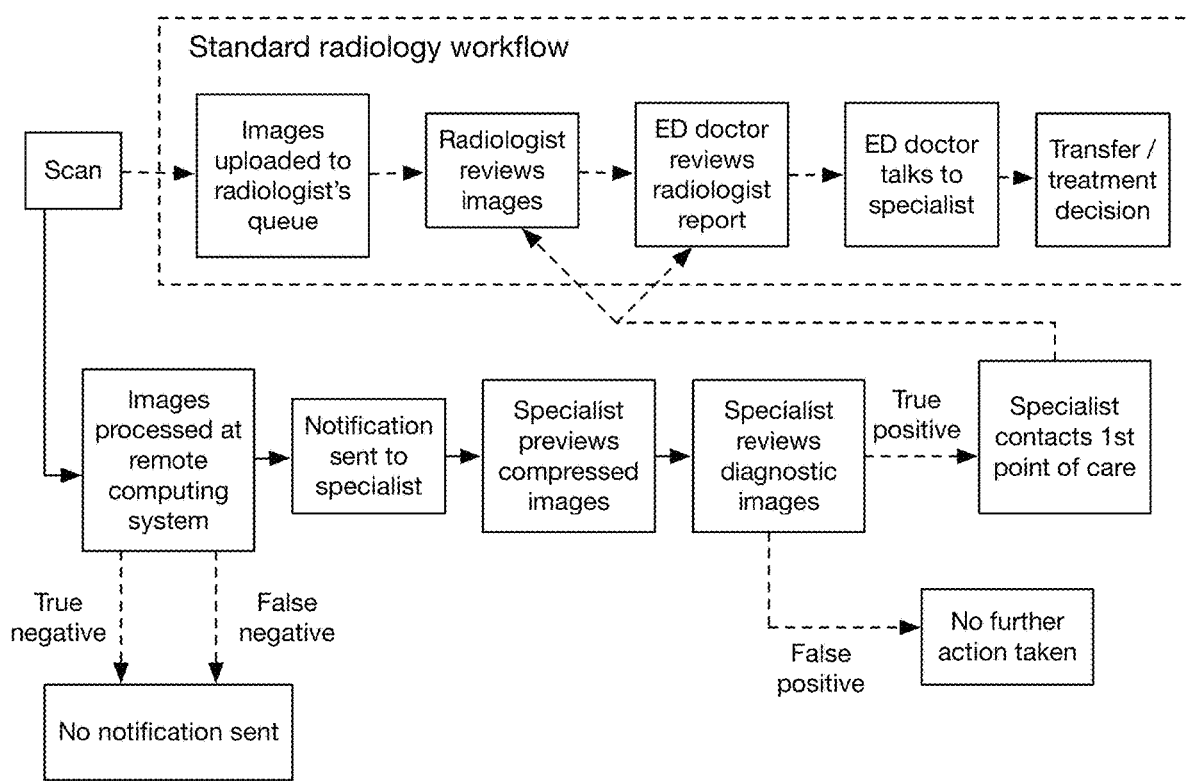
FIG. 3 depicts a variation of a method for computer-aided triage.
Figure 4:
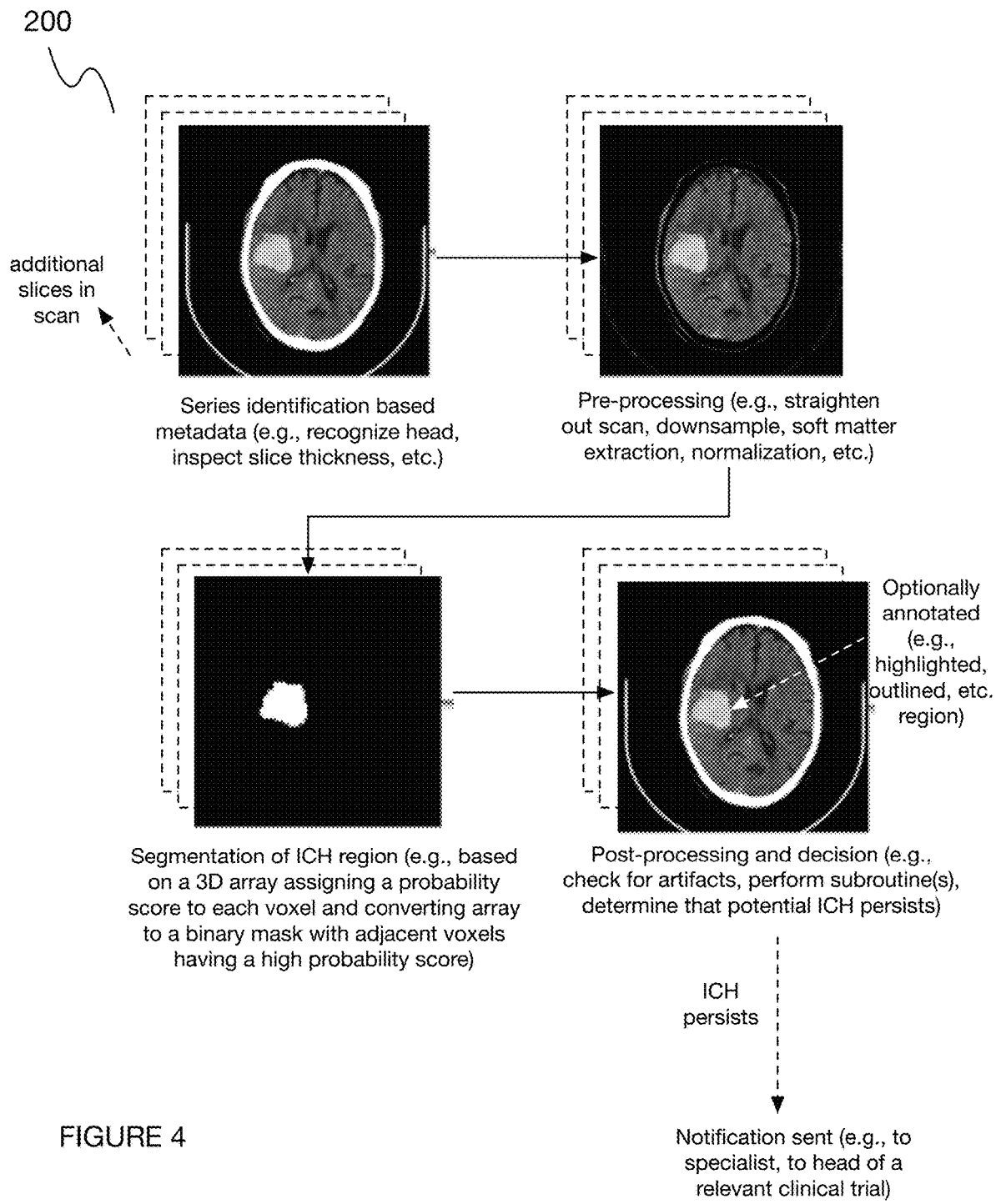
FIG. 4 depicts a variation of determining a patient condition during a method for computer-aided triage.

The method 200 is preferably performed separate from but in parallel with (e.g., contemporaneously with, concurrently with, etc.) a standard radiology workflow (e.g., as shown in FIG. 3), but can additionally or alternatively be implemented within a standard workflow, be performed at a separate time with respect to a standard workflow, or be performed at any suitable time.

The method 200 can be partially or fully implemented with the system 100 or with any other suitable system.

The method 200 functions to improve communication across healthcare facility networks (e.g., stroke networks, spokes and hubs, etc.) and decrease the time required to transfer a patient having a suspected time-sensitive condition (e.g., brain condition, stroke, hemorrhagic stroke, hemorrhage, intracerebral hemorrhage (ICH), ischemic stroke, large vessel occlusion (LVO), cardiac event, trauma, etc.) from a first point of care (e.g., spoke, non-specialist facility, stroke center, ambulance, etc.) to a second point of care (e.g., hub, specialist facility, comprehensive stroke center, etc.), wherein the second point of care refers to a healthcare facility equipped to treat the patient. In some variations, the second point of care is the first point of care, wherein the patient is treated at the healthcare facility to which he or she initially presents.

The method 200 preferably functions as a parallel workflow tool, wherein the parallel workflow is performed contemporaneously with (e.g., concurrently, during, partially during) a standard radiology workflow (e.g., radiologist queue), but can additionally or alternatively be implemented within a standard workflow (e.g., to automate part of a standard workflow process, decrease the time required to perform a standard workflow process, etc.), be performed during a workflow other than a radiology workflow (e.g., during a routine examination workflow), or at any other suitable time.

The method 200 is preferably performed in response to a patient presenting at a first point of care. The first point of care can be an emergency setting (e.g., emergency room, ambulance, imaging center, etc.) or any suitable healthcare facility, such as those described previously. The patient is typically presenting with (or suspected to be presenting with), equivalently referred to herein as an acute setting, a time-sensitive condition, such as a neurovascular condition (e.g., stroke, ischemic stroke, occlusion, large vessel occlusion (LVO), thrombus, aneurysm, etc.), cardiac event or condition (e.g., cardiovascular condition, heart attack, etc.), trauma (e.g., acute trauma, blood loss, etc.), or any other time-sensitive (e.g., life-threatening) condition. In other variations, the method is performed for a patient presenting to a routine healthcare setting (e.g., non-emergency setting, clinic, imaging center, etc.), such as for routine testing, screening, diagnostics, imaging, clinic review, laboratory testing (e.g., blood tests), or for any other reason.

Any or all of the method can be performed using any number of machine learning (e.g., deep learning) or computer vision modules. Each module can utilize one or more of: supervised learning (e.g., using logistic regression, using back propagation neural networks, using random forests, decision trees, etc.), unsupervised learning (e.g., using an Apriori algorithm, using K-means clustering), semi-supervised learning, reinforcement learning (e.g., using a Q-learning algorithm, using temporal difference learning), and any other suitable learning style. Each module of the plurality can implement any one or more of: a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a deep learning algorithm (e.g., a restricted Boltzmann machine, a deep belief network method, a convolution network method, a stacked auto-encoder method, etc.), a dimensionality reduction method (e.g., principal component analysis, partial lest squares regression, Sammon mapping, multidimensional scaling, projection pursuit, etc.), an ensemble method (e.g., boosting, boostrapped aggregation, AdaBoost, stacked generalization, gradient boosting machine method, random forest method, etc.), and any suitable form of machine learning algorithm. Each module can additionally or alternatively be a: probabilistic module, heuristic module, deterministic module, or be any other suitable module leveraging any other suitable computation method, machine learning method, or combination thereof.

Each module can be validated, verified, reinforced, calibrated, or otherwise updated based on newly received, up-to-date measurements; past measurements recorded during the operating session; historic measurements recorded during past operating sessions; or be updated based on any other suitable data. Each module can be run or updated: once; at a predetermined frequency; every time the method is performed; every time an unanticipated measurement value is received; or at any other suitable frequency. The set of modules can be run or updated concurrently with one or more other modules, serially, at varying frequencies, or at any other suitable time. Each module can be validated, verified, reinforced, calibrated, or otherwise updated based on newly received, up-to-date data; past data or be updated based on any other suitable data. Each module can be run or updated: in response to determination of an actual result differing from an expected result; or at any other suitable frequency.

4.1 Method—Receiving a Data Packet Associated with a Patient and Taken at a First Point of Care S205

The method 200 includes receiving a data packet associated with a patient and taken at a first point of care S205, which functions to collect data relevant to assessing a patient condition.

The data is preferably received at a router no, wherein the router is in the form of a virtual machine operating on a computing system (e.g., computer, workstation, quality assurance (QA) workstation, reading workstation, PACS server, etc.) coupled to or part of an imaging modality (e.g., CT scanner, MRI scanner, etc.), or any other suitable router. Additionally or alternatively, data can be received at a remote computing system (e.g., from an imaging modality, from a database, a server such as a PACS server, an internet search, social media, etc.), or at any other suitable computing system (e.g., server) or storage site (e.g., database). In some variations, for instance, a subset of the data (e.g., image data) is received at the router while another subset of the data (e.g., patient information, patient history, etc.) is received at a remote computing system. In a specific example, the data subset received at the router is eventually transmitted to the remote computing system for analysis.

S205 is preferably performed in response to (e.g., after, in real time with, substantially in real time with, with a predetermined delay, with a delay of less than 10 seconds, with a delay of less than 1 minute, at the prompting of a medical professional, etc.) the data (e.g., each of a set of instances) being generated at the imaging modality. Additionally or alternatively, S205 can be performed in response to a set of multiple instances being generated by the imaging modality (e.g., after a partial series has been generated, after a full series has been generated, after a study has been generated, etc.), in response to a metadata tag being generated (e.g., for an instance, for a series, for a study, etc.), in response to a trigger (e.g., request for images), throughout the method (e.g., as a patient's medical records are accessed, as information is entered a server, as information is retrieved from a server, etc.), or at any other suitable time.

S205 can be performed a single time or multiple times (e.g., sequentially, at different times in the method, once patient condition has progressed, etc.). In one variation, each instance is received (e.g., at a router, at a remote computing system, etc.) individually as it is generated. In a second variation, a set of multiple instances (e.g., multiple images, full series, etc.) are received together (e.g., after a scan has completed, after a particular anatomical component has been imaged, etc.).

The router (e.g., virtual machine, virtual server, application running on the image sampling system or a computing system connected to the image sampling system, etc.) can be continuously 'listening' (e.g., operating in a scanning mode, receiving mode, coupled to or include a radio operating in a suitable mode, etc.) for information from the imaging modality, can receive information in response to prompting of a healthcare facility worker, in response to a particular scan type being initiated (e.g., in response to a head CTA scan being initiated), or in response to any other suitable trigger.

Image data is preferably received at the router (e.g., directly, indirectly, etc.) from the imaging modality (e.g., scanner) at which the data was generated. Additionally or alternatively, image data or any other data can be received from any computing system associated with the healthcare facility's PACS server, any DICOM-compatible devices such as a DICOM router, or any other suitable computing system. The image data is preferably in the DICOM format but can additionally or alternatively include any other data format.

In addition to or alternative to image data, the data can include blood data, electronic medical record (EMR) data, unstructured EMR data, health level 7 (HL7) data, HL7 messages, clinical notes, or any other suitable data related to a patient's medical state, condition, or medical history.

The data preferably includes a set of one or more instances (e.g., images), which can be unorganized, organized (e.g., into a series, into a study, a sequential set of instances based on instance creation time, acquisition time, image position, instance number, unique identification (UID), other acquisition parameters or metadata tags, anatomical feature or location within body, etc.), complete, incomplete, randomly arranged, or otherwise arranged.

Each instance preferably includes (e.g., is tagged with) a set of metadata associated with the image dataset, such as, but not limited to: one or more patient identifiers (e.g., name, identification number, UID, etc.), patient demographic information (e.g., age, race, sex, etc.), reason for presentation (e.g. presenting symptoms, medical severity score, etc.), patient history (e.g., prior scans, prior diagnosis, prior medical encounters, etc.), medical record (e.g. history of present illness, past medical history, allergies, medications, family history, social history, etc.), scan information, scan time, scan type (e.g., anatomical region being scanned, scanning modality, scanner identifier, etc.), number of images in scan, parameters related to scan acquisition (e.g., timestamps, dosage, gurney position, scanning protocol, contrast bolus protocol, etc.), image characteristics (e.g., slice thickness, instance number and positions, pixel spacing, total number of slices, etc.), or any other suitable information.

In some variations, any or all of the data (e.g., image data) is tagged with metadata associated with the standard DICOM protocol.

In some variations, one or more tags is generated and/or applied to the data after the data is generated at an imaging modality. In some examples, the tag is an identifier associated with the $1^{st}$ point of care (e.g., $1^{st}$ point of care location, imaging modality identifier, etc.), which can be retrieved by a $2^{nd}$ point of care in order to locate the patient (e.g., to enable a quick transfer of the patient, to inform a specialist of who to contact or where to reach the patient, etc.).

Additionally or alternatively, image data can be received without associated metadata (e.g., metadata identified later in the method, dataset privately tagged later with metadata later in the method, etc.)

In a first set of variations for detecting ICH, metadata of images are checked for metadata inclusion criteria, including/indicating any or all of: a CT scan of the head, an axial series, a slice thickness within a supported range, the absence of missing slices, aligned instance numbers and positions, patient age above a minimum threshold (e.g., between 0 and 10, between 10 and 20, between 20 and 30, above 30, etc.), consistent pixel spacing, a total number of slices within a predetermined range (e.g., between 18 and 25), and/or any other suitable metadata inclusion criteria.

Data can be received (e.g., at the router) through a wired connection (e.g., local area network (LAN) connection), wireless connection, or through any combination of connections and information pathways.

In a first variation (e.g., for a patient presenting with symptoms of an ICH), S205 includes receiving an NCCT scan of a patient's head. In a preferred specific example of this variation, the NCCT scan includes an axial series of images (equivalently referred to herein as instances and/or slices), each of the images corresponding to an axial thickness between 2.5 and 5 millimeters, wherein the axial series includes no missing slices and wherein the slices are properly ordered (e.g., instance numbers and positions aligned).

4.2 Method—Transmitting Data to a Remote Computing System S208

The method can include transmitting data to remote computing system (e.g., remote server, PACS server, etc.) S208, which functions to enable remote processing of the data, robust process, or fast processing (e.g., faster than analysis done in clinical workflow, faster than done in a standard radiology workflow, processing less than 20 minutes, less than 10 minutes, less than 7 minutes, etc.) of the dataset.

The data (e.g., image data, image data and metadata, etc.) is preferably transmitted to a remote computing system from a router (e.g., virtual machine operating on a scanner) connected to a computing system (e.g., scanner, workstation, PACS server, etc.) associated with a healthcare facility, further preferably where the patient first presents (e.g., $1^{st}$ point of care), but can additionally or alternatively be transmitted from any healthcare facility, computing system, or storage site (e.g., database).

Each instance (e.g., image) of the dataset (e.g., image dataset) is preferably sent individually as it is generated at an imaging modality and/or received at a router, but additionally or alternatively, multiple instances can be sent together after a predetermined set (e.g., series, study, etc.) has been generated, after a predetermined interval of time has passed (e.g., instances sent every 10 seconds), upon the prompting of a medical professional, or at any other suitable time. Further additionally or alternatively, the order in which instances are sent to a remote computing system can depend one or more properties of those instances (e.g., metadata). S208 can be performed a single time or multiple times (e.g., after each instance is generated).

S208 can include transmitting all of the dataset (e.g., image dataset and metadata), a portion of the dataset (e.g., only image dataset, subset of image dataset and metadata, etc.), or any other information or additional information (e.g., supplementary information such as supplementary user information).

The data is preferably transmitted through a secure channel, further preferably through a channel providing error correction (e.g., over TCP/IP stack of 1$^{st}$ point of care), but can alternatively be sent through any suitable channel.

S208 can include any number of suitable sub-steps performed prior to or during the transmitting of data to the remote computing system. These sub-steps can include any or all of: encrypting any or all of the dataset (e.g., patient information) prior to transmitting to the remote computing system, removing information (e.g., sensitive information), supplementing the dataset with additional information (e.g., supplementary patient information, supplemental series of a study, etc.), compressing any or all of the dataset, or performing any other suitable process.

4.3 Method—Preparing a Data Packet for Analysis S210

The method 200 preferably includes preparing a data packet S210 for analysis (e.g., pre-processing), which can function to pre-process any or all of the data packet, eliminate an irrelevant (e.g., incorrectly labeled, irrelevant anatomical region, etc.) or unsuitable data packet from further analysis, or perform any other suitable function.

S210 can optionally include one or more registration steps (e.g., image registration steps), which function to align, scale, calibrate, or otherwise adjust the set of images. Alternatively, the images can proceed to future processes without being registered. The registration step can be performed through registering any or all of the set of images either in their raw form or processed form (e.g., soft matter extracted from set of instances) to a reference set of images (e.g., reference series); alternatively, the registration step can be performed in absence of comparing the present set of images with a reference set of images. The registration is preferably performed in response to a data packet being filtered through a set of exclusion criteria, but can additionally or alternatively be performed prior to or in absence of the filtering, multiple times throughout the method, or at any other suitable time.

The registration step can be intensity-based, feature-based, or otherwise configured, and can include any or all of: point-mapping, feature-mapping, or any other suitable process. Additionally or alternatively, it can be based on a deep neural network. The reference set of images is preferably determined from a training set but can alternatively be determined from any suitable dataset, computer-generated, or otherwise determined. The reference series can be selected for any or all of orientation, size, three-dimensional positioning, clarity, contrast, or any other feature. In one variation, a references series is selected from a training set, wherein the reference series is selected based on a feature parameter (e.g., largest feature size such as largest skull, smallest feature size, etc.) and/or a degree of alignment (e.g., maximal alignment, alignment above a predetermined threshold, etc.). Additionally or alternatively, any other criteria can be used to determine the reference series, the reference series can be randomly selected, formed from aggregating multiple sets of images (e.g., multiple patient series), or determined in any other suitable way. In some variations, the registration is performed with one or more particular software packages (e.g., SimpleElastix). In a specific example, the registration is performed through affine registration (e.g., in SimpleElastix) with a set of predetermined (e.g., default) parameters and iterations (e.g., 4096 iterations, between 3000 and 5000 iterations, above 1000 iterations, above 100 iterations, etc.) in each registration step. In another example, the affine transformation is computed using a deep neural network.

Preprocessing the images preferably includes resizing the images (e.g., through downsampling, lossless compression, lossy compression, etc.), which functions to compress the images and can subsequently enable and/or shorten the time of transfer of data between points of the system (e.g., from a virtual machine to a remote computing system, from a remote computing system to a mobile device and/or workstation, etc.). Additionally, in variations involving trained deep learning models, resizing the images can function to enable fast training convergence while maintaining high resolution. Preprocessing the images can further include straightening out the images (e.g., rotating a portion of the image, translating a portion of the image, etc.). In a first variation, registering a set of brain slices (e.g., from an NCCT) includes one or both of straightening out the brain region and downsampling each image (e.g., from 512×512 to 96×96 or 256×256).

S210 can include windowing (equivalently referred to herein as clipping) the image data, which can function to increase the image contrast of a predetermined (e.g., desired) range (window) of pixel/voxel values (e.g., Hounsfield units), eliminate irrelevant information (e.g., information not corresponding to regions of interest/potential user conditions) from further processing, and/or perform any other suitable function. The threshold values (e.g., HU values) determining the window range can optionally be determined based on any or all of: the type of scan (e.g., contrast, non-contrast, CT, NCCT, MRI, etc.), the body region scanned (e.g., head), suspected condition (e.g., type of brain hemorrhage, ICH, LVO, etc.), patient demographics and/or metadata (e.g., age, gender, etc.), and/or any other suitable information. Additionally or alternatively, the threshold values can be constant for all images.

In preferred variations (e.g., for detecting brain conditions), the range of HU values that are retained for processing ranges from a Hounsfield unit just below that corresponding to soft matter to a Hounsfield unit just above that corresponding to bone. Additionally or alternatively, a window can be shifted with respect to this (e.g., anything below bone), narrowed with respect to this (e.g., only encompassing brain tissue), broadened with respect to this, or otherwise selected.

In specific examples, the information retained has HU values based on a window level of 1000 and a window width of 2000 (e.g., HU values between 0 and 2000).

S210 can further include an effective and/or actual removal (e.g., assignment of a pixel value of zero, actual removal through cropping, etc.) of one or more regions of the image, which is preferably performed after and based on a windowing process (e.g., as described above), but can additionally or alternatively be performed prior to a windowing process, in absence of a windowing process, in a later process (e.g., after a segmentation process), or otherwise performed. In one variation, a set of "white" regions (e.g., regions having a pixel/voxel value of 255, regions having a pixel/voxel value above a predetermined threshold, etc.) are assigned a pixel/voxel value of zero, which—in combination with a windowing process as described above—can function to result in the extraction of only soft matter (e.g., brain matter, blood, cerebral fluid, etc.); this can equivalently be referred to herein as skull stripping. Additionally or alternatively, any other regions can be effectively and/or actually removed in any suitable way (e.g., through photomasks, dilation, erosion, etc.).

S210 can further include the normalization of any or all of the image data, which can function to enable the comparison of multiple instances with each other, the comparison of one series with a different series (e.g., the series of a previously-taken brain scan, the series of one patient with a reference series, the series of a first patient that that of a second patient, etc.), enable faster training convergence of deep learning models in processing, and/or perform any other suitable function. In one variation, the set of voxels in the image data are normalized such that the voxels have a predetermined mean Hounsfield unit value (e.g., 24.5 HU, less than 24.5 HU, greater than 24.5 HU, etc.) and a predetermined standard deviation Hounsfield unit value (e.g., 39.5 HU, less than 39.5 HU, greater than 39.5 HU, etc.). Additionally or alternatively, the image data can be normalized in any other suitable way with respect to any suitable parameter. In specific examples, the image data is normalized by dividing by a fixed number (e.g., between 200 and 300, 250, 255, 260, etc.).

S210 can optionally include organizing the set of instances, preferably into a series, but additionally or alternatively into a study, or any other suitable grouping of images. The organization is preferably performed in response to generating a set of instances (e.g., at an imaging modality), but can additionally or alternatively be performed in response to receiving a set of instances at a location (e.g., router, remote computing system, server such as a PACS server, etc.), at the request of an individual (e.g., healthcare worker), in response to a trigger, in response to any other pre-processing step, or at any other suitable time.

In some variations, the method includes excluding a data packet (e.g., set of instances) from further processing if one or more of a set of metadata are not satisfied, such as, but not limited to, the metadata listed above.

In a specific example, a bone mask is determined and defined as a set of voxels having an HU value above a predetermined threshold (e.g., 750 HU, 700 HU, 800 HU, between 600 HU and 900 HU, etc.). The bone mask is then dilated with a series of kernels of increasing size until it completely encloses a set of voxels of low HU values (e.g., less than the predetermined threshold), thereby defining a soft matter mask. The soft matter mask is dilated to compensate for the dilation of the bone mask. If the process of defining the soft matter mask fails, this can indicate that the skull has undergone a craniotomy, which in some cases can be used in determining a diagnosis, informing a contact or second point of care, or in any other point in the method. Once the soft matter mask is dilated, the mask can then be applied to the set of instances (e.g., organized set of instances, series, etc.), and the HU value of voxels outside of the mask is set to zero.

In a first set of variations, S210 includes resizing/downsampling the set of images (e.g., from 512×512 to 256×256); removing irrelevant information from the set of images based on Hounsfield Unit windowing process (e.g., clipping voxels corresponding to HU value below 1000 and above 2000); and normalizing the HU values of the image set voxels (e.g., by dividing by a fixed number).

4.4 Method—Checking for a Suspected Condition Associated with the Data Packet S220

Figure 9:
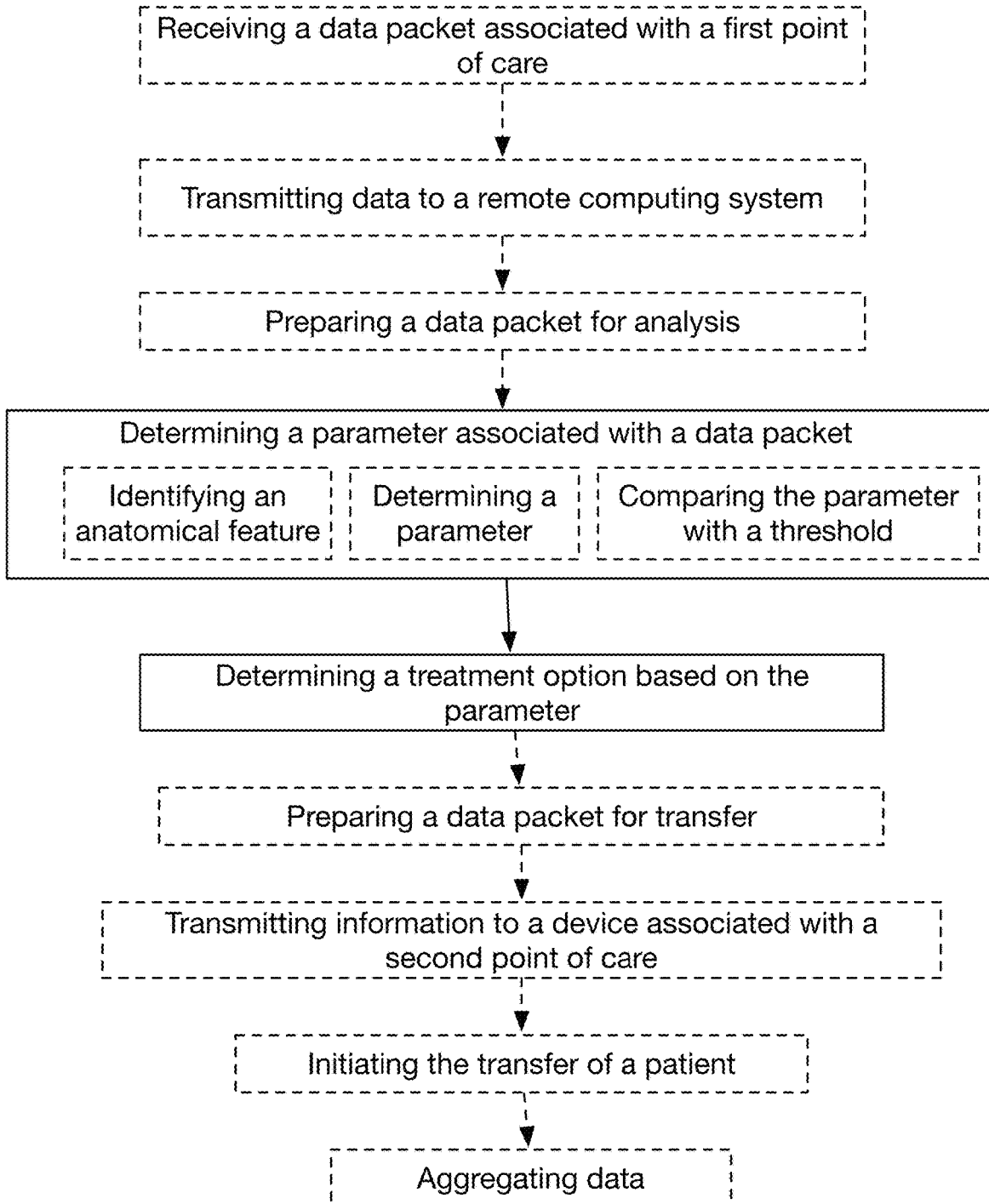
FIG. 9 depicts a variation of the method.

The method 200 includes checking for a suspected condition and optionally one or more parameters of the suspected condition (e.g., as shown in FIG. 9) associated with the data packet S220, which functions to inform the remaining processes of the method 200. Additionally or alternatively, S220 can function to reduce the time to transfer a patient to a second point of care, halt progression of the condition, or perform any other suitable function. S220 is preferably fully performed at a remote computing system (e.g., remote server, cloud-based server, etc.), further preferably a remote computing system having a graphics processing unit (GPU), but can additionally or alternatively be partially performed at any suitable remote computing system, be partially or fully performed at a local computing system (e.g., workstation), server (e.g., PACS server), at a processor of a user device, or at any other system. S220 is preferably partially or fully performed using software including one or more algorithms, further preferably one or more multi-step algorithms containing steps that are either trained (e.g., trained through machine learning, trained through deep learning, continuously trained, etc.) or non-trained (e.g., rule-based image processing algorithms or heuristics). Additionally or alternatively, any software can be implemented.

In preferred variations, S220 includes processing an input produced in S210 with one or more deep learning models, preferably deep CNNs, but additionally or alternatively any other suitable deep learning models. The deep learning models are preferably trained on training data including at least images corresponding to (e.g., containing, diagnosed as, testing positive for, etc.) the condition being tested for in the method 200 and images absent of (e.g., testing negative for) the condition. In preferred variations, the deep learning models are additionally iteratively trained based on the results of an earlier version of the model(s) (e.g., through one or more boosting algorithms). In specific examples, the results of a first set of models which indicated the presence of a condition (tested positive) and were later found to not contain the condition (false positives) are used as training data to minimize the occurrence of false positive determinations. In specific examples, the false positive inputs are labeled (e.g., as mistakenly labeled, as a common mistake, as negative, as a false positive, etc.) and trained on these more difficult cases.

The method can optionally additionally or alternatively include producing augmented data for training one or more models, which can include any or all of: random rotations (e.g., 2D rotations) of images (e.g., rotations between 45 degrees counterclockwise and 45 degrees clockwise), random shifts (e.g., in the 2D plane) of images (e.g., shifts of 25% or less in a horizontal axis, shifts of 16% or less in a horizontal axis, shifts of less than 15% in a vertical axis, shifts of less than 12% in a vertical axis, etc.), 2D scale changes (e.g., in the range of 0.8×-1.2×), horizontal flips, the addition of image noise, and/or any other suitable modifications of images.

S220 can optionally include producing and/or receiving a second image set, such as a modified version (e.g., mirror image horizontally, mirror image vertically, rotated, translated, etc.) of the image set produced in S210, which can function to increase the accuracy and/or likelihood of detecting a patient condition. In some variations, such as those in which a symmetric anatomical region (e.g., brain) is being analyzed, this can improve the likelihood that the patient condition is accurately detected (e.g., as the present images could most closely relate to a brain condition occurring in an opposite brain hemisphere in the training data). The results of the first and second set of images can be averaged, combined in a weighted fashion, used as inputs for an algorithm or model, compared and the highest value ultimately selected for use in subsequent processes of the method, and/or otherwise used. In specific examples, the pre-processed brain images produced in S210 and a horizontal flip of these images are fed through a feed-forward deep convolutional neural network (CNN) (e.g., trained to segment hyper-attenuated regions consistent with ICH), wherein the predictions of the scan and its horizontal flip are averaged.

S220 preferably includes identifying (e.g., locate, isolate, measure, quantify, etc.) and segmenting an affected brain region (e.g., brain region saturated with blood, blood region, etc.) within one or more of the set of instances, thereby indicating a hemorrhagic brain condition (e.g., ICH) or at least a potential hemorrhagic brain condition. In preferred variations, the hemorrhagic brain condition able to be detected includes at least an intracerebral hemorrhage (e.g., an intraparenchymal hemorrhage, a subarachnoid hemorrhage, etc.); an intraventricular hemorrhage; an extradural hemorrhage; a subdural hemorrhage; any combination of hemorrhages; and/or any other suitable hemorrhage. Additionally or alternatively, any other brain conditions (e.g., vessel occlusion) or other health condition (e.g., cardiac condition, lung condition, etc.) can be detected. This can be performed through any number of computer vision techniques, such as object recognition, object identification, object detection, or any other form of image analysis.

In some variations, identifying an affected brain region (e.g., blood region) is performed at least partially through image segmentation, wherein the segmentation includes any or all of: thresholding, clustering methods, dual clustering methods, compression-based methods, histogram-based methods, region-growing methods, partial differential equation-based methods, variational methods, graph partitioning methods, watershed transformations, model based segmentation, multi-scale segmentation, semi-automatic segmentation, trainable segmentation, or any suitable form of segmentation. The method can additionally or alternatively include any number of segmentation post-processing steps, such as thresholding, connectivity analyses, or any other processing. The segmentation is preferably performed with a convolutional neural network (CNN), further preferably feed-forward deep CNN (e.g., using three-dimensional convolutions, two-dimensional convolutions, etc.), but can additionally or alternatively be performed using any suitable algorithm or process.

The segmentation is preferably performed for an input including a set of pre-processed image slices (e.g., according to S210 as described above), further preferably consecutive pre-processed image slices. Additionally or alternatively, a segmentation of un-processed (e.g., raw), unordered, and/or a set of slices missing intermediate slices, can be performed.

The segmentation preferably includes assigning a probability score (e.g., between 0 and 1) to each base unit (e.g., pixel, voxel, etc.) of the input, which indicates a likelihood that the base unit represents a part of the brain condition (e.g., ICH) or set of brain conditions being tested for. A segmentation region (e.g., initial segmentation region, final segmentation region, etc.) is then formed from the base units having a probability score above a predetermined threshold.

In one variation, the segmentation of a set of NCCT scan slices functions to segment hyper-attenuated brain regions which are consistent with a hemorrhage (e.g., ICH). In a specific example, a 3D array is formed from the set of scan slices, the 3D array containing a set of probability values between 0 and 1 for each of the set of voxels in a 3D representation of the scan slices, the probability values corresponding to a likelihood that each voxel corresponds to a hemorrhage/hemorrhaged region (equivalently referred to herein as a hyperdensity) of the brain (e.g., region of brain tissue containing blood). A set of voxels (e.g., contiguous voxels, connected voxels, bordering voxels, etc.), preferably adjacent (e.g., contiguous) voxels (but alternatively non-adjacent or partially adjacent voxels), having a probability of at least a predetermined threshold (e.g., 0.5, 0.6, 0.7, 0.8, 0.9, etc.) represents a region suspected of having a hemorrhage. The probabilistic output of the network is converted into a binary mask defined as all voxels having a probability greater than this threshold (e.g., 0.5, 0.7, between 0.4 and 0.8, etc.), which forms the segmentation.

The probability threshold can optionally be dependent on any number of features of the segmentation and/or images, such as any or all of: the location of the segmented region (e.g., intraparenchymal, intraventricular, epidural, subdural, subarachnoid, etc.), the suspected condition (e.g., and a severity of the condition being tested for), metadata, and/or any other suitable features. Alternatively, the probability threshold can be constant.

In a set of variations, a voxel probabilistic output is converted to a binary mask defined to be all voxels having a probability greater than a threshold, preferably a threshold that provides a favorable compromise between sensitivity and specificity. If specific examples, the threshold is equal to 50%. Additionally or alternatively, the threshold can be greater than 50% for higher specificity (e.g., between 50% and 60%, 60%, 70%, 80%, 90%, between 50% and 100%, etc.), less than 50% for higher sensitivity (e.g., between 40% and 50%, 40%, 30%, 20%, 10%, greater than 0%, etc.), and/or any other percentage for any suitable objective.

Additionally or alternatively, probabilities from multiple voxels can be aggregated (e.g., averaged) and compared with a threshold, a minimum number of high probabilities can need to be reached, and/or any probabilities can be examined in any suitable ways.

S220 further preferably includes evaluating one or more exclusion criteria in the segmentation and/or any other part of the image data, which can function to verify that the image data is relevant for evaluation in the rest of the method, save time and/or resources by eliminating irrelevant scans, check for a particular set of false positives (e.g., artifacts, eliminate one or more categories of false positives while still maintaining an overall high percentage of false positives, eliminate one or more categories of false positives while still maintaining an overall high percentage of false negatives, minimizing a number of false positives, etc.), route a set of instances corresponding to one or more exclusion criteria to another workflow in a healthcare facility, or perform any other suitable function. In some variations, for instance, a set of exclusion criteria are evaluated, which function to keep "close call" false positives (e.g., questionable pathologies, affected brain tissue, etc.) while eliminating false positives caused by non-physiological events (e.g., metal artifact, poor image quality, etc.). Additionally or alternatively, exclusion criteria are evaluated to minimize an overall number of false positives, thereby minimizing, for instance, unnecessary interruptions to specialists and/or any other number of recipients (e.g., clinical trial principal investigators). Alternatively, the method can partially or fully process all sets of instances. The exclusion criteria can be: learned (e.g., from false positives and/or false negatives; labeled training data; training such as iterative training of one or more deep learning models with images corresponding to false positives; etc.); manually determined (e.g., be a set of rules, a decision tree, a heuristic, etc.); or be otherwise determined.

Evaluating exclusion criteria preferably includes checking for any or all of: the presence of an artifact (e.g., metallic artifact, aneurysm clip, etc.) in one or more of the set of images, improper timing at which the set of images were taken at an imaging modality (e.g., premature timing, improper timing of a bolus, etc.), one or more incomplete regions (e.g., features, anatomical features, etc.) in the set of images (e.g., incomplete skull, incomplete vessel, incomplete soft matter region, etc.), an incorrect scan type or body part (e.g., non-head CT scan, non-contrast CT scan, etc.), poor image quality (e.g., blurry images, low contrast, etc.), movement of the patient during the scan (e.g., manifesting as bright streaks in one or more images), or any other suitable exclusion criteria.

In one variation, a set of images are evaluated to determine if an artifact is present, wherein the set of images is excluded from further steps in the method if an artifact is found. In a specific example, the method includes inspecting the HU values of voxels in a soft matter mask, wherein voxels having a value above a predetermined threshold (e.g., 3000 HU, between 2000 and 4000 HU, etc.) are determined to be a metallic artifact (e.g., aneurysm clip).

Evaluating exclusion criteria can include a first subroutine, which functions to evaluate the set of instances on a per-slice basis, wherein each slice having been processed through a segmentation process (e.g., as described above, producing a set of regions having the same or similar probability values, etc.) is divided into connected components (e.g., regions made up of contiguous voxels having the same or a similar probability value, regions made up of contiguous voxels having a probability above a predetermined threshold, etc.). The connected components can then be eliminated from further processing (e.g., discarded) based on a set of thresholds in any number of a set of categories.

The set of categories preferably includes a size category, wherein connected components (e.g., segmentations) are evaluated based on any or all of: area (e.g., number of pixels), volume (e.g., volume in mL, number of voxels etc.), one or more characteristic dimensions (e.g., maximum dimension, minimum dimension, length, width, maximum length, maximum width, thickness, radius, diameter, etc.), or any other suitable size category. The size can be compared with a threshold, wherein if the size is below the threshold (e.g., indicating an artifact, indicating noise, etc.), the component is eliminated from further processing and/or consideration. Additionally or alternatively, if the size is above a threshold (e.g., indicating an image quality issue, indicating an ICH too severe for intervention, etc.), the component can be eliminated from further processing and/or consideration; if the size is within a range of thresholds, the component can be eliminated from further processing and/or consideration; if the size is outside a range of thresholds, the component can be eliminated from further processing and/or consideration; or the component can be otherwise evaluated and/or further processed.

In a first variation (e.g., ICH), a size of the segmented region is compared with a minimum volume threshold, wherein if the segmented region size is below the minimum volume threshold, the segmented region is eliminated from further consideration of the condition, and wherein if the segmented region size is above the minimum volume threshold, the segmented region continues to further processing and/or results in the determination of the suspected condition. In specific examples, the minimum volume threshold is 0.1 mL. Additionally or alternatively, the volume threshold can be greater than 0.1 mL (e.g., 0.2 mL, 0.3 mL, 0.4 mL, 0.5 mL, between 0.5 and 1 mL, 1 mL or greater, etc.), less than 0.1 mL (e.g., 0.09 mL, 0.08 mL, 0.07 mL, 0.06 mL, 0.05 mL, between 0 and 0.05 mL, etc.), and/or have any other suitable value. Further additionally or alternatively, the size threshold can include a 2D size threshold (e.g., per slice), 1D size threshold (e.g., largest length of segmentation in a slice, largest width of segmentation in a slice, thickness, etc.), and/or any other suitable thresholds.

In a second variation, additional or alternative to the first, the size category can be configured to determine if a suspected blood region is instead a movement of the patient while in the scanner, which can manifest itself in bright, "blood-like" streaks in the image. If it's determined that the size (e.g., area, volume, etc.) of a suspected bleed is above a predetermined threshold, yet only shows up on a number of images below a predetermined threshold (e.g., only one slice, less than 3 slices, less than 10 slices, etc.), then it can likely instead be attributed to the patient moving during the scan.

The set of categories can optionally include a location category, wherein connected components (e.g., segmentations) are evaluated based on their proximity to another component, such as another anatomical component (e.g., bone, skull, etc.), a particular brain region or brain feature (e.g., particular sulcus, lobe, covering, etc.), an image feature (e.g., an image edge, etc.), or any other component or general location. In the event that the relative location (e.g., distance, proximity, etc.) is below a threshold (indicating that the component is too close), the component can be discarded. In some variations involving brain hemorrhage detection, this can be used to categorize a suspected brain hemorrhage as being one of: an intracerebral hemorrhage (e.g., an intraparenchymal hemorrhage, a subarachnoid hemorrhage, etc.); an intraventricular hemorrhage; an extradural hemorrhage; a subdural hemorrhage; any combination of hemorrhages.

Additionally or alternatively, any other categories and associated thresholds can serve as exclusion category in the first subroutine.

In one variation, the first subroutine includes dividing each slice of the segmentation mask into connected components, wherein connected components smaller than a predetermined volume (e.g., 0.4 milliliters [mL], less than 0.4 mL, greater than 0.4 mL, etc.) and less than a predetermined number of voxels away from a bone voxel (e.g., less than 3 voxels away; less than a threshold greater than 3 voxels away; less than a threshold less than 3 voxels away; etc.) are eliminated from future analysis (e.g., discarded).

Evaluating exclusion criteria can further include a performing a second subroutine, which functions to evaluate the set of instances on a volumetric basis, wherein the entire segmentation mask is divided into 3D connected components. The second subroutine is preferably performed after the first subroutine has been performed (e.g., after a first set of components have been eliminated, after a set of slices has been eliminated, etc.). Additionally or alternatively, the second subroutine can be performed in parallel with the first subroutine, prior to the first subroutine, in absence of the first subroutine, and/or at any suitable time. Further additionally or alternatively, the method can include any other subroutine(s).

The second subroutine can evaluate the components based on similar and/or the same categories as described for the first subroutine; additionally or alternatively, any other suitable categories and associated thresholds can be evaluated. These can include any number of size categories, such as, but not limited to: volume, thickness (e.g., anatomical thickness, number of slices, number of consecutive slices, a thickness extracted from the number of slices, etc.), a characteristic dimension (e.g., width, length, diameter, etc.), curvature, or any other suitable size parameter. These can further include any number of location categories (e.g., proximity to another anatomical region, location as described above), or any other suitable categories In a first variation of the second subroutine, a segmentation mask is divided into connected components in 3D, wherein the thickness of a connected component is defined as the total number of consecutive slices containing voxels belonging to that connected component. Components with a thickness below a predetermined threshold (e.g., thickness of 1, thickness below 2, thickness below 3, thickness below 5, thickness below 10, etc.) are eliminated from further analysis.

Additionally or alternatively, any other subroutine(s) can be performed. In variations involving multiple subroutines (e.g., to analyze a set of images in multiple different dimensions, to analyze a set of images based on multiple different categories, to analyze a set of images based on increasingly more stringent criteria, to analyze a set of images based on increasingly less stringent criteria, to analyze a set of images based on multiple different procedures, etc.), the subroutines can be performed in series (e.g., using the output of a previous subroutine as the input of the present subroutine, using the same input as the previous subroutine, etc.), in parallel, or in a combination of series and parallel. In preferred variations, each subsequent subroutine builds upon the previous (e.g., uses the results of the previous subroutine to check for further exclusion criteria). In alternative variations, a set of subroutines are performed independently of each other and the results combined (e.g., consolidated, weighted, etc.) to determine a final output.

Based on the outcome of the segmentation and/or evaluation of exclusion criteria (or alternatively the original segmentation), one or more determinations of the patient condition can be made and/or ruled out. The condition typically refers to a predicted (e.g., hypothesized, assumed, having a probability above a predetermined threshold, etc.) patient condition or diagnosis (e.g., ICH, LVO, aneurysm, stroke, etc.) but can additionally or alternatively include a severity (e.g., based on a predetermined severity scale), an urgency, or any other characteristic.

In a first set of variations, if the connected component, which is formed from the connecting of voxels having a probability above a predetermined threshold (e.g., 50%), is above a predetermined size threshold (e.g., volume threshold above 0.1 mL), the condition is determined to be suspected.

In a second set of variations, if the connected component (e.g., after performing the subroutines) contains at least one voxel marked as a critical voxel (e.g., corresponding to ICH, corresponding to another brain condition, etc.), it is determined that the patient has the potential condition (e.g., ICH). Additionally or alternatively, any suitable threshold(s) can be used (e.g., more than one voxel marked as critical, between 1 and 20 voxels marked as critical, less than 20 voxels marked as critical, etc.).

The determination preferably triggers one or more outcomes (e.g., as described below), but can additionally or alternatively prompt further analysis, such as the determination of one or more associated parameters. In variations of ICH, for instance, these can include any or all of: an amount of compromised brain matter (e.g., hyperdense, containing blood of at least a predetermined threshold density, region proximal to an occluded vessel, etc.), an amount of uncompromised brain matter, the particular affected region (e.g., brain territory, brain lobe, etc.), the function of the affected region (e.g., motor control, memory, emotion, etc.), a trajectory of the affected region (e.g., rate of spreading, blood flow rate, time until critical, time until fatal, etc.), or any other suitable parameter.

Additionally or alternatively, S220 can include any other processes performed in any suitable order.

4.5 Method—In an Event that the Suspected Condition is Detected, Determining a Recipient Based on the Suspected Condition S230

The method includes in an event that the suspected condition is detected, determining a recipient based on the suspected condition S230, which functions to facilitate the treatment (e.g., triage, acceptance into a clinical trial, etc.) of the patient.

S230 can additionally, alternatively, and/or equivalently include determining a treatment option, preferably in the event that a condition is detected (e.g., based on a comparison with a threshold, based on a binary presence, etc.) but can additionally or alternatively determine a treatment option when a condition is not detected, when an analysis is inconclusive, or in any suitable scenario. S230 can function to match the patient with a specialist, initiate the transfer of a patient to a $2^{nd}$ point of care (e.g., specialist facility), initiate the transfer of a specialist to a $1^{st}$ point of care, initiate treatment of a patient (e.g., surgery, stent placement, mechanical thrombectomy, etc.) within the $1^{st}$ point of care, initiate the matching of a patient to a clinical trial, or perform any other suitable function. In some variations, the treatment option is a $2^{nd}$ point of care, wherein it is determined (e.g., suggested, assigned, etc.) that the patient should be treated at the $2^{nd}$ point of care. Additionally or alternatively, the treatment option can be a procedure (e.g., surgical procedure, surgical clipping, mechanical thrombectomy, placement of an aneurysm coil, placement of a stent, retrieval of a thrombus, stereotactic radiosurgery, etc.), treatment (e.g., tissue plasminogen activator (TPA), pain killer, blood thinner, etc.), recovery plan (e.g., physical therapy, speech therapy, etc.), or any other suitable treatment.

The treatment is preferably determined based on a parameter determined from the data packet (e.g., binary presence of a condition, comparison of a parameter with a threshold, etc.), but can additionally or alternatively be determined based on additional data, such as patient information (e.g., demographic information, patient history, patient treatment preferences, etc.), input from one or more individuals (e.g., power of attorney, attending physician, emergency physician, etc.), a consensus reached by multiple recipients of a notification (e.g., majority of members of a care team, all members of a care team, etc.), or any other suitable information.

S230 is preferably at least partially performed with software operating at the remote computing system (e.g., remote server) but can additionally or alternatively be performed at a remote computing system separate from a previous remote computing system, a local computing system (e.g., local server, virtual machine coupled to healthcare facility server, computing system connected to a PACS server), or at any other location.

S230 is preferably performed after a patient condition has been determined during the method 200. Additionally or alternatively, S230 can be performed after a patient condition has been determined in an alternative workflow (e.g., at the $1^{st}$ point of care, at a radiologist workstation during a standard radiology workflow, in the case of a false negative, etc.), prior to or absent the determination of a patient condition (e.g., based on an input from a healthcare worker at the remote computing system, when patient is admitted to $1^{st}$ point of care, etc.), multiple times throughout the method (e.g., after a first treatment option fails, after a first specialist is unresponsive, such as after a threshold amount of time, such as 30 seconds, 1 minute, 2 minutes, etc.), or at any other time during the method.

S230 preferably determines a treatment option with a lookup table located in a database accessible at remote computing system (e.g., cloud-computing system). Additionally or alternatively, a lookup table can be stored at a healthcare facility computing system (e.g., PACS server), in storage at a user device, or at any other location.

In other variations, the treatment option can be determined based on one or more algorithms (e.g., predictive algorithm, trained algorithm, etc.), one or more individuals (e.g., specialist, care team, clinical trial coordinator, etc.), a decision support tool, a decision tree, a set of mappings, a model (e.g., deep learning model), or through any other process or tool.

The lookup table preferably correlates a $2^{nd}$ point-of-care (e.g., healthcare facility, hub, physician, specialist, neurointerventionist, etc.), further preferably a specialist or contact (e.g., administrative worker, emergency room physician, etc.), with a patient condition (e.g., presence of an ICH, presence of an LVO, presence of a pathology, severity, etc.), but can additionally or alternatively correlate any treatment option with the patient condition. The lookup table can further additionally or alternatively correlate a treatment option with supplementary information (e.g., patient history, demographic information, heuristic information, etc.).

The contact (e.g., healthcare provider, neuro-interventional specialist, principal investigator, stroke care team member, principal investigator, clinical trial enrollment committee, etc.) is preferably a healthcare worker, but can additionally or alternatively be any individual associated with the treatment of the patient and/or be associated with any healthcare facility (e.g., prior healthcare facility of patient, current healthcare facility, recommended healthcare facility) related to the patient. The contact is further preferably a specialist (e.g., neuro-interventional specialist, neurosurgeon, neurovascular surgeon, general surgeon, cardiac specialist, etc.) but can additionally or alternatively include an administrative worker associated with a specialist, multiple points of contact (e.g., ranked order, group, etc.), or any other suitable individual or group of individuals. The contact is preferably associated with a hub facility, wherein the hub facility is determined as an option for second point of care, but can additionally or alternatively be associated with a spoke facility (e.g., current facility, future facility option, etc.), an individual with a relation to the patient (e.g., family member, employer, friend, acquaintance, emergency contact, etc.), or any other suitable individual or entity (e.g., employer, insurance company, etc.). Additionally or alternatively, the contact can be an individual associated with a clinical trial (e.g., principal investigator at a $1^{st}$ point of care, principal investigator at a $2^{nd}$ point of care, approval/enrollment committee to approve a patient for a clinical trial, etc.), and/or any other suitable individual.

The lookup table is preferably determined based on multiple types of information, such as, but not limited to: location information (e.g., location of a $1^{st}$ point of care, location of a $2^{nd}$ point of care, distance between points of care, etc.), temporal information (e.g., time of transit between points of care, time passed since patient presented at $1^{st}$ point of care, etc.), features of condition (e.g., size of occlusion, severity of condition, etc.), patient demographics (e.g., age, general health, history, etc.), specialist information (e.g., schedule, on-call times, historic response time, skill level, years of experience, specialty procedures, historic success or procedures, etc.), healthcare facility information (e.g., current number of patients, available beds, available machines, etc.), but can additionally or alternatively be determined based on a single type of information or in any other suitable way. Information can be actual, estimated, predicted, or otherwise determined or collected.

In some variations, the method 200 includes transmitting information (e.g., patient condition, data determined from analysis, optimal set of instances, series, data packet, etc.) to the computing system associated with the lookup table.

4.6 Method—Preparing a Data Packet for Transfer S240

The method 200 can include preparing a data packet for transfer, which can function to produce a compressed data packet, partially or fully anonymize a data packet (e.g., to comply with patient privacy guidelines, to comply with Health Insurance Portability and Accountability Act (HIPAA) regulations, to comply with General Data Protection Regulation (GDRP) protocols, etc.), minimize the time to transfer a data packet, annotate one or more images, or perform any other suitable function. Additionally or alternatively, any or all of a data packet previously described can be transferred.

The data packet is preferably transferred (e.g., once when data packet is generated, after a predetermined delay, etc.) to a contact, further preferably a specialist (e.g., associated with a $2^{nd}$ point of care, located at the $1^{st}$ point of care, etc.), but can additionally or alternatively be sent to another healthcare facility worker (e.g., at $1^{st}$ point of care, radiologist, etc.), an individual (e.g., relative, patient, etc.), a healthcare facility computing system (e.g., workstation), a server or database (e.g., PACS server), or to any other suitable location.

S240 preferably includes compressing a set of images (e.g., series), but can additionally or alternatively leave the set of images uncompressed, compress a partial set of images (e.g., a subset depicting the condition), or compress any other part of a data packet. Compressing the data packet functions to enable the data packet to be sent to, received at, and viewed on a user device, such as a mobile device. Compressing the data packet can include any or all of: removing a particular image region (e.g., region corresponding to air, region corresponding to hard matter, region without contrast dye, irrelevant anatomical region, etc.), thresholding of voxel values (e.g., all values below a predetermined threshold are set to a fixed value, all values above a predetermined threshold are set to a fixed value, all values below −500 HU are set to −500, all voxel values corresponding to a particular region are set to a fixed value, all voxels corresponding to air are set to a predetermined fixed value, etc.), reducing a size of each image (e.g., scale image size by factor of 0.9, scale image size by factor of 0.7, scale image size by factor of 0.5, scale image size by a factor between 0.1 and 0.9, reduce image size by a factor of 4, etc.), or through any other compression method.

In one variation, the reduction in size of a set of images can be determined based on one or more memory constraints of the receiving device (e.g., user device, mobile device, etc.).

In some variations, such as those involving a patient presenting with a brain condition (e.g., ICH, LVO), the images taken at an imaging modality (e.g., CT scanner) are compressed by determining an approximate or exact region in each image corresponding to air (e.g., based on HU value, based on location, based on volume, etc.) and setting the air region (e.g., voxels corresponding to the air region, pixels corresponding to the air region, etc.) to have a fixed value. Additionally or alternatively, any non-critical region (e.g., bone, unaffected region, etc.) or other region can be altered (e.g., set to a fixed value, removed, etc.) during the compression. In a specific example, for instance, a set of voxels corresponding to air are set to all have a common fixed value (e.g., an upper limit value, a lower limit value, a value between 0 and 1, a predetermined value, etc.).

In some variations, S240 includes identifying an optimal visualization to be transmitted (e.g., from a remote computing system) and received (e.g., at a user device), which functions to prepare an optimal output for a $2^{nd}$ point of care (e.g., specialist), reduce the time required to review the data packet, bring attention to the most relevant image data, or to effect any other suitable outcome.

In some variations, this involves a reverse registration process. In a specific example, for instance, this is done through maximum intensity projection (MIP), where an optimal range of instances is determined based on which images contain the largest percentage of the segmented anatomical region of interest in a MIP image.

Additionally or alternatively, S240 can include removing and/or altering (e.g., encrypting) metadata or any unnecessary, private, confidential, or sensitive information from the data packet. In some variations, patient information (e.g., patient-identifiable information) is removed from the data packet in order to comply with regulatory guidelines. In other variations, all metadata are extracted and removed from the data packet.

S240 can optionally include annotating one or more images in the data packet, which can function to draw attention to one or more features of the images, help a specialist or other recipient easily and efficiently assess the images, and/or perform any other suitable functions.

Figure 8:
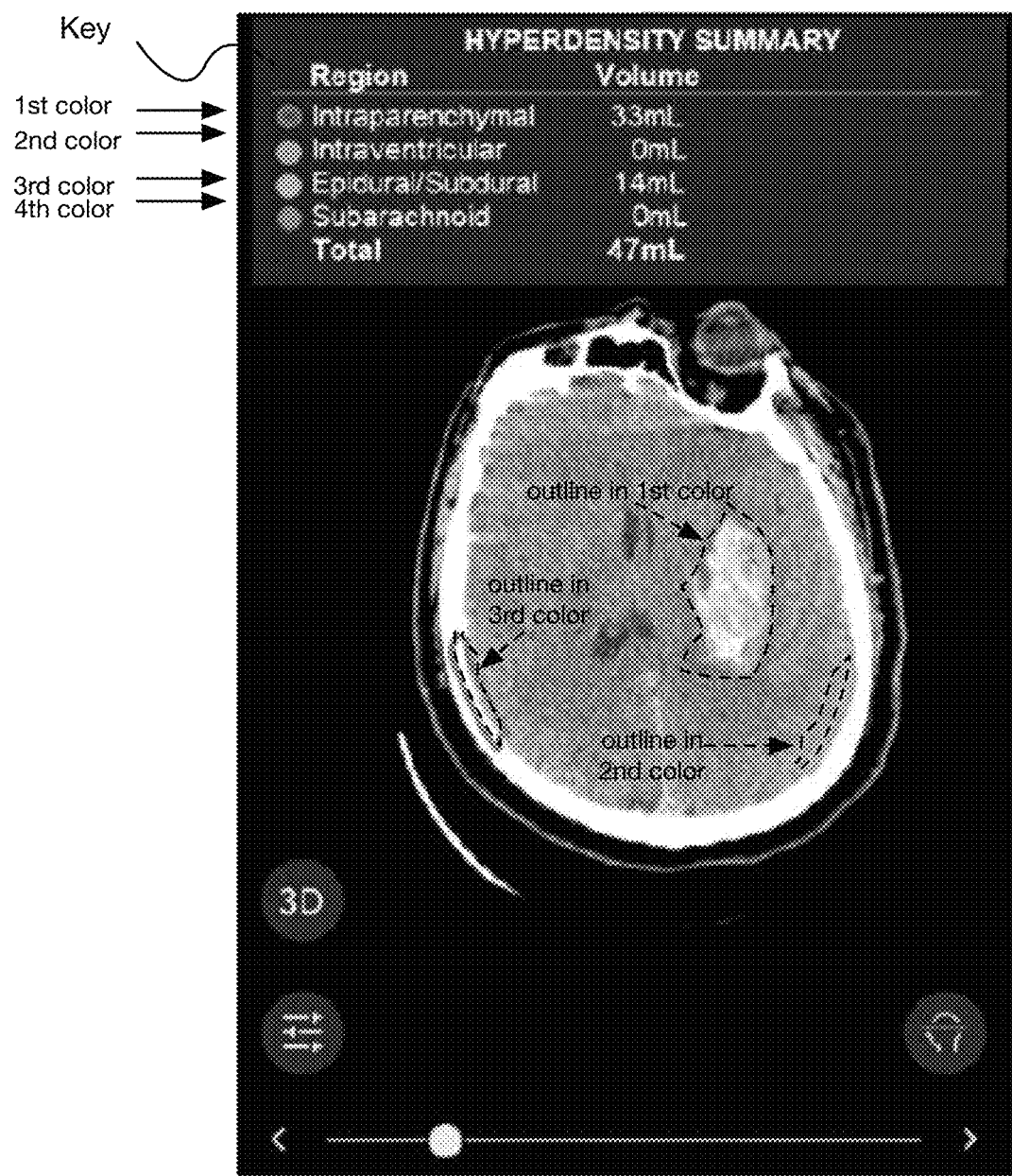
FIG. 8 depicts a variation of an annotated image transmitted to a recipient.

Annotating the images can optionally include adding (e.g., assigning, overlaying, etc.) one or more visual indicators (e.g., labels, text, arrows, highlighted or colored regions, measurements, etc.) to one or more images. The incorporation of the visual indicators can be determined based on any or all of: the suspected condition (e.g., type of visual indicators designated for the condition based on a lookup table), one or more thresholds (e.g., size thresholds), features of the suspected condition/pathology (e.g., location of hemorrhage within brain), preferences (e.g., specialist preferences, point of care preferences, etc.), guidelines (e.g., patient privacy guidelines), the results of one or more deep learning models, and/or any other suitable factors or information. In variations with visual indicators, a table/key can optionally be provided (e.g., as shown in FIG. 8) to explain the visual indicators, which can include any or all of: a color key defining what colors correspond to; one or more parameters associated with an indicated region or feature (e.g., volume of hyperdensities identified in each region); one or more parameters associated with the image(s) as a whole (e.g., total hyperdensity volume measured across all regions, number of regions indicated, etc.); and/or any other suitable information.

Images can additionally or alternatively be annotated with one or more metrics, such as one or more parameters (e.g., size as described above); scores (e.g., a clinical score, a severity score, etc.); instructions (e.g., recommended intervention); and/or any other suitable information. In some variations for annotating images associated with a suspected brain hemorrhage (e.g., ICH), an Alberta Stroke Program Early CT Score (ASPECTS), which is a quantitative score used to assess ischemic damage and predict irreversible injury, can be calculated and annotated on one or more images. Additionally or alternatively, any other suitable score can be calculated and provided to (e.g., in a message, email, etc.) a recipient.

Additionally or alternatively to being annotated on an image, any or all of the annotations can be provided in a separate notification, such as a message, document, and/or provided in any other suitable way.

The annotations are preferably determined automatically (e.g., at a remote computing system implementing the deep learning models, at a client application, at a mobile device executing a client application, etc.), but can additionally or alternatively be determined manually, verified manually, or otherwise determined.

In some variations of hemorrhage detection, for instance, a size of the hemorrhage (e.g., volume) has been found to be helpful in decision-making for the specialist (e.g., determining whether or not to intervene, determining a type of intervention, etc.) and is indicated to the specialist on one or more images transmitted to him or her. In specific examples (e.g., as shown in FIG. 8, the hemorrhage region is indicated by (e.g., highlighted in, outlined in, etc.) one of a set of colors, wherein the color indicates a type of hemorrhage (e.g., intraparenchymal, intraventricular, epidural/subdural, subarachnoid, etc.). Additionally, a calculated volume of the region is preferably provided. Additionally or alternatively, any other suitable information can be provided. In other specific examples, for instance a color can indicate any or all of: a size, such as a range of volumes corresponding to a suspected condition (e.g., hemorrhage); a type of condition; a severity of a condition; and/or any other information.

S240 can optionally include prescribing a subset of images to be viewed by the recipient and/or an order in which images should be viewed (e.g., the particular image shown first to the recipient upon opening a client application in response to receiving a notification, the image shown in the thumbnail of a notification, the only image or subset of images sent, etc.). This can include, for instance, selecting the image or images indicating the suspected condition (e.g., all slices containing the suspected condition, a single slice containing the suspected condition, the slice containing the largest cross section of a suspected condition, the slice containing an important or critical feature of the suspected condition, etc.) for viewing by the recipient. In specific examples, the recipient (e.g., specialist) is sent a notification wherein when the recipient opens the notification on a device (e.g., mobile device), the image corresponding to the suspected condition is shown first (and optionally corresponds to a thumbnail image shown to the recipient in the notification).

The notification(s) and/or image(s) provided to a recipient are preferably provided within a threshold time period from the time in which the patient is imaged (e.g., 15 minutes, between 10 and 15 minutes, 10 minutes, 9 minutes, 8 minutes, 7 minutes, 6 minutes, 5 minutes, 3 minutes, 2 minutes, 1 minute, etc.), but can additionally or alternatively be provided in another suitable time frame (e.g., greater than 15 minutes), prior to a next action in the standard of care (e.g., prior to a decision is made by a radiologist in a parallel workflow), and/or at any other time(s).

In some variations, S240 includes storing a dataset (e.g., at a remote server, at a local server, at a PACS server, etc.). In one example, metadata are extracted from the image data and stored separately from image data in a relational database. In another example, any or all of the data packet are stored (e.g., temporarily, permanently, etc.) to be used in one or more future analytics processes, which can function to improve the method, better match patients with suitable treatment options, or for any other suitable purpose.

S240 can optionally include applying a low bandwidth implementation process, which can function to reduce the time until a specialist receives a first piece of data or data packet (e.g., an incomplete series, incomplete study, single instance, single image, optimal image, image showing occlusion, etc.), reduce the processing required to inform a specialist of a potential patient condition, reduce the amount of data required to be reviewed by a specialist, reduce the amount of data being transmitted from a remote computing system to a mobile device, or perform any other suitable function. The low bandwidth implementation process can include any or all of: organizing (e.g., chunking) data (e.g., chunking a series of images based on anatomical region), reordering data (e.g., reordering slices in a CT series), transmitting a portion (e.g., single image, single slice, etc.) of a data packet (e.g., series, study, set of images, etc.) to a device (e.g., user device, mobile device, healthcare facility workstation, computer, etc.), sending the rest of the data packet (e.g., only in response to a request, after a predetermined time has passed, once the data packet has been fully processed, etc.), or any other process. In a specific example, for instance, the image data (e.g., slices) received at a remote computing system from a scanner are chunked, reordered, and a subset of slices (e.g., a single slice) is sent to the device associated with a specialist (e.g., prior to sending a remaining set of slices, in absence of sending a remaining set of slices, etc.).

In some variations, S240 includes implementing a buffering protocol, which enables a recipient (e.g., specialist) to start viewing images (e.g., on a mobile device) prior to all of the images being loaded at the device (e.g., user device, mobile device, etc.) at which the recipient is viewing images. Additionally or alternatively, the buffering protocol can include transmitting images to the recipient in batches, annotating images in batches, or otherwise implementing a buffering protocol.

Additionally or alternatively, S240 can include any other suitable steps performed in any suitable order.

The method can additionally or alternatively include any other suitable sub-steps for preparing the data packet.

In a first set of variations, S240 includes determining a subset of one or more images conveying information related to a suspected patient condition (e.g., showing the presence of the condition, showing the largest region of the condition, showing a particular feature of the condition, etc.); optionally annotating the images (e.g., to point out the condition); and preparing a notification to be sent to the specialist, wherein the notification instructs the specialist to view at least the subset of images and optionally includes a thumbnail depicting one of the set of images which the specialist can view prior to viewing the images.

4.7 Method—Transmitting Information to a Device Associated with the $2^{nd}$ Point of Care S250

Figure 6:
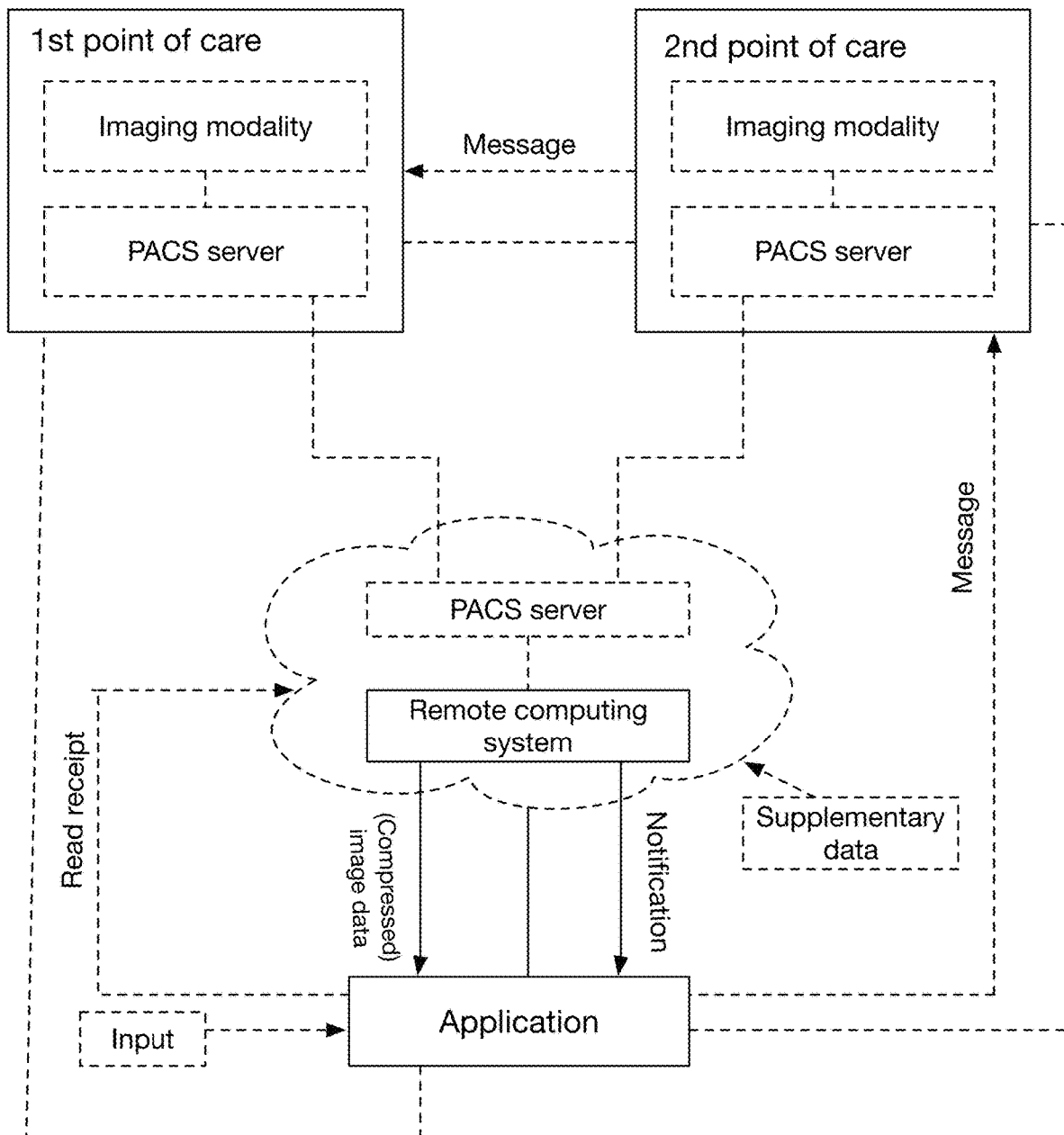
FIG. 6 depicts a variation of a method for computer-aided triage.

Transmitting information to a device associated with the $2^{nd}$ point of care (e.g., specialist, contact, etc.) S250 (e.g., as shown in FIG. 6) functions to initiate a pull from a $1^{st}$ point of care to a $2^{nd}$ point of care, which can decrease time to care, improve quality of care (e.g., better match between patient condition and specialist), or have any other suitable outcome. Preferably, the $2^{nd}$ point of care is a hub facility (e.g., specialist facility, interventional center, comprehen-sive stroke center, etc.). In some variations, the $1^{st}$ point of care (e.g., healthcare facility at which patient initially presents) also functions as the $2^{nd}$ point of care, such as when a suitable specialist is associated with the $1^{st}$ point of care, the $1^{st}$ point of care is a hub (e.g., specialist facility, interventional center, comprehensive stroke center, etc.), it is not advised to transfer the patient (e.g., condition has high severity based on a calculated severity score), or for any other reason.

S250 is preferably performed after (e.g., in response to) a $2^{nd}$ point of care is determined, but can additionally or alternatively be performed after a data packet (e.g., compressed data packet, encrypted data packet, etc.) has been determined, multiple times throughout the method (e.g., to multiple recipients, with multiple data packets, with updated information, after a predetermined amount of time has passed since a notification has been sent to a first choice specialist, etc.), or at any other time during the method 200.

The device is preferably a user device, further preferably a mobile device. Examples of the user device include a tablet, smartphone, mobile phone, laptop, watch, wearable device (e.g., glasses), or any other suitable user device. The user device can include power storage (e.g., a battery), processing systems (e.g., CPU, GPU, memory, etc.), user outputs (e.g., display, speaker, vibration mechanism, etc.), user inputs (e.g., a keyboard, touchscreen, microphone, etc.), a location system (e.g., a GPS system), sensors (e.g., optical sensors, such as light sensors and cameras, orientation sensors, such as accelerometers, gyroscopes, and altimeters, audio sensors, such as microphones, etc.), data communication system (e.g., a WiFi module, BLE, cellular module, etc.), or any other suitable component.

The device is preferably associated with (e.g., owned by, belonging to, accessible by, etc.) a specialist or other individual associated with the $2^{nd}$ point of care, but can additionally or alternatively be associated with an individual or computing system at the $1^{st}$ point of care, the patient, or any other suitable individual or system.

In one variation, the device is a personal mobile phone of a specialist. In another variation, the device is a workstation at a healthcare facility (e.g., first point of care, second point of care, etc.).

In some variations, information is sent to multiple members (e.g., all members) of a care team or clinical trial team, such as the care team who is treating, may treat the patient, or and/or will treat the patient. This can enable the care team members to do any or all of: make a decision together (e.g., transfer decision, treatment decision, etc.); communicate together (e.g., through the client application); and/or perform any other function.

The information preferably includes a data packet, further preferably the data packet prepared in S240. Additionally or alternatively, the information can include a subset of a data packet, the original data packet, any other image data set, or any other suitable data. The information further preferably includes a notification, wherein the notification prompts the individual to review the data packet at the device (e.g., a message reciting "urgent: please review!"). The notification can optionally include a thumbnail with a selected image (e.g., image indicating patient condition), which a recipient can view quickly, such as prior to the recipient unlocking device to which the notification is sent. Additionally or alternatively, the notification can prompt the individual to review data (e.g., original data packet, uncompressed images, etc.) at a separate device, such as a workstation in a healthcare facility, a PACS server, or any other location. Further additionally or alternatively, the notification can include any suitable information, such as, but not limited to: instructions (e.g., for treating patient, directions for reaching a healthcare facility), contact information (e.g., for emergency physician at first point of care, administrative assistant, etc.), patient information (e.g., patient history), or any other suitable information.

The notification preferably includes an SMS text message but can additionally or alternatively include a message through a client application (e.g., as described above, image viewing application, medical imaging application, etc.), an email message (e.g., de-identified email), audio notification or message (e.g., recording sent to mobile phone), push notification, phone call, a notification through a medical platform (e.g., PACS, EHR, EMR, healthcare facility database, etc.), pager, or any other suitable notification.

One or more features of a notification can optionally convey a severity of the patient condition and/or an urgency of receiving a response from a recipient, which can function to adequately alert the recipient and properly prioritize care of the patient (e.g., relative to other patients). In specific examples, for instance, an audio cue associated with a notification indicates an urgency of treating a patient, so that a recipient of the message knows to immediately review the images and triage the patient.

The information is preferably sent to the device through a client application executing on the user device but can additionally or alternatively be sent through a messaging platform, web browser, or other platform. In some variations, the information is sent to all devices (e.g., mobile phone, smart watch, laptop, tablet, workstation, etc.) associated with the recipient (e.g., specialist), such as all devices executing the client application associated with the recipient, which functions to increase the immediacy in which the recipient is notified.

In one variation, S240 includes preparing a notification to be sent to a device (e.g., user device, mobile device, etc.) associated with a recipient (e.g., a specialist), wherein the notification includes a thumbnail indicating a selected image (e.g., compressed image showing a suspected condition), along with a message instructing the recipient to review the images in a client application, and optionally the original images at a workstation afterward. In a first set of specific examples, upon detection that a read receipt has not been received (e.g., at the remote computing system) in a predetermined amount of time (e.g., 30 seconds, 1 minute, 2 minutes, between 0 seconds and 2 minutes, 3 minutes, between 2 minutes and 3 minutes, 5 minutes, greater than 5 minutes, less than 10 minutes, etc.), a second notification is transmitted to a second recipient (e.g., a second specialist). In a second set of specific examples, sending the notification further triggers and/or enables communication to be established among multiple members of a care team (e.g., a stroke team), such as through a messaging component of the client application, wherein the images can be viewed and discussed among the care team members. In a third set of specific examples, a notification is sent to specialist on a mobile device of the specialist, compressed images are previewed on the specialist mobile device, and the specialist is notified as being responsible for viewing non-compressed images on a diagnostic viewer and engaging in appropriate patient evaluation and relevant discussion with a treating physician before making care-related decisions or requests.

In a second variation, S240 includes preparing a notification to be sent to a clinical trial research coordinator, such as a principal investigator, wherein the notification indicates that the patient is a potential candidate for a clinical trial (e.g., based on the detection of a suspected condition, based on a set of clinical trial inclusion criteria, etc.). In specific examples, a notification can be sent (e.g., automatically, triggered by the principal investigator, etc.) to a members of a clinical trial committee (e.g., physician committee), wherein approval is granted by the committee members (e.g., a majority, all, at least one, a predetermined number or percentage, etc.), such as through the client application.

4.8 Method—Receiving an Input from the Recipient

The method 200 can include receiving an input from the recipient, which functions to determine a next step for the patient, and can include any or all of: a confirmation of the suspected condition; a rejection of the suspected condition (e.g., false positive); an acceptance by a specialist and/or care team (e.g., stroke team) to treat the patient (e.g., at a $1^{st}$ point of care, at a $2^{nd}$ point of care, etc.); a rejection of a specialist and/or care team to treat the patient; a read receipt and/or an indication of a lack or a read receipt within a predetermined time threshold; an approval to enroll the patient in a clinical trial; additional clinical information entered by a physician and/or other user; and/or any other suitable input.

In some variations, a notification is sent in S250 which prompts the individual to provide an input, wherein the input can indicate that the individual will view, has viewed, or is in the process of viewing the information (e.g., image data), sees the presence of a condition (e.g., true positive, serious condition, time-sensitive condition, etc.), does not see the presence of a condition (e.g., false positive, serious condition, time-sensitive condition, etc.), has accepted treatment of the patient (e.g., swipes right, swipes up, clicks a check mark, etc.), has denied treatment of the patient (e.g., swipes left, swipes down, clicks an 'x', etc.), wants to communicate with another individual (e.g., healthcare worker at $1^{st}$ point of care), such as through a messaging platform (e.g., native to the device, enabled by the client application, etc.), or any other input. In some variations, one or more additional notifications are provided to the individual (e.g., based on the contents of the input), which can be determined by a lookup table, operator, individual, decision engine, or other tool. In one example, for instance, if the individual indicates that the condition is a true positive, information related to the transfer of the patient (e.g., estimated time of arrival, directions to the location of the patient, etc.) can be provided (e.g., in a transfer request, wherein patient transfer to a specified location, such as the $2^{nd}$ point of care, can be initiated upon transfer request receipt). In some variants, the data (e.g., images) are displayed on the user device (e.g., mobile device, workstation) in response to user interaction with the notification (e.g., in response to input receipt). However, the input can trigger any suitable action or be otherwise used.

Additionally or alternatively, an input can automatically be received from the client application, such as a read receipt when the individual has opened the data packet, viewed the notification, or interacted with the client application in any other suitable way. In one example, if a read receipt is not received (e.g., at the remote computing system) from the device within a predetermined amount of time (e.g., 10 seconds), a second notification and/or data packet (e.g., compressed set of images) are sent to a second individual (e.g., second choice specialist based on a lookup table).

In some variations, various outputs can be sent from the client application (e.g., at the user device) to one or more recipients (e.g., to a second user device, client application on a work station, on a computing system, etc.), such as recipients associated with a first point of care (e.g., radiologists, emergency physicians, etc.). The outputs can be determined based on the inputs received at the client application associated with the individual (e.g., acceptance of case, verification of true positive, etc.), based on a lookup table, or otherwise determined. The outputs preferably do not alter the standard radiology workflow (e.g., are not shared with radiologists; radiologists are not notified), which functions to ensure that the method 200 is a true parallel process, and that the standard radiology workflow results in an independent assessment of the patient, but can additionally or alternatively cut short a workflow, bring a specialist in on the patient case earlier than normal, or affect any other process in a healthcare facility.

The outputs can include any or all of: the suspected condition, parameters (e.g., volume of an ICH) and/or scores (e.g., severity score, urgency score, etc.) associated with the suspected condition; the selection of one or more recipients of a notification (e.g., established and/or proposed care team of the patient); a proposed and/or confirmed intervention for the patient (e.g., type of procedure); an updated status (e.g., location, health status, intervention status, etc.) of one or more patients (e.g., a centralized list of all patients being reviewed by and/or treated by a specialist; a consent of the patient (e.g., for a clinical trial); an estimated parameter of the patient (e.g., estimated time of arrival at a second point of care); and/or any other suitable outputs.

4.9 Method—Initiating Treatment of the Patient

The method can additionally or alternatively include initiating treatment (e.g., transfer) of the patient, wherein the treatment can include any or all of the treatment options described above, such as ay or all of: a point of care (e.g., remain at $1^{st}$ point of care, be transferred to a $2^{nd}$ point of care, etc.) at which the patient will be treated; a procedure to treat the suspected condition; a specialist and/or care team to be assigned to the patient; a clinical trial in which to enroll the patient; and/or any other suitable treatments.

In variations involving recommending the patient for a clinical trial, initiating treatment of the patient can include receiving a recommendation that the patient be considered for a clinical and/or research trial, based on one or more of: a suspected clinical condition of the patient (e.g., ICH), patient information (e.g., demographic information), a patient's willingness or potential willingness to participate, and/or any other suitable information. Initiating the recommendation can include transmitting any or all of the notifications described above (e.g., text message, call, email, etc.) to a specialist involved in the clinical and/or research trial, a specialist who has actively turned on notifications for clinical trial recruitment, a researcher, a research principal investigator, an administrative assistant, the patient himself, or any other suitable entity or individual.

4.8 Method—Aggregating Data S260

The method 200 can optionally include any number of sub-steps involving the aggregation of data involved in and/or generated during the method 200, which can function to improve future iterations of the method 200 (e.g., better match patients with a specialist, decrease time to treat a patient, increase sensitivity, increase specificity, etc.). The aggregated data is preferably used in one or more analytics steps (e.g., to refine a treatment option, make a recommendation for a drug or procedure, etc.), but can additionally or alternatively be used for any other suitable purpose.

In some variations, for instance the outcomes of the patients examined during the method 200 are recorded and correlated with their corresponding data packets, which can be used to assess the success of the particular treatment options chosen and better inform treatment options in future cases.

4.9 Variations

In one variation of the system 100, the system includes a router no, which operates at a computing system at a $1^{st}$ point of care and receives image data from an imaging modality. The router transmits the image data to a remote computing system, wherein a series of algorithms (e.g., machine learning algorithms) are performed at the remote computing system, which determines a hypothesis for whether or not a suspected condition (e.g., ICH) is present based on the image data and/or any associated metadata. Based on the determination, a contact is determined from a lookup table (e.g., in storage at the remote computing system), wherein the contact is notified at a user device (e.g., personal device) and sent image data through a client application executing on the user device. One or more inputs from the contact at the application can be received at the remote computing system, which can be used to determine a treatment option (e.g., next point of care) for the patient. However, the system and/or components thereof can be used in any other suitable manner.

In a first variation of the method 200, the method functions to augment a standard radiology workflow operating in parallel with the method, which can include any or all of: at a remote computing system (e.g., remote from the first point of care), receiving a set of images (e.g., of a brain of the patient), wherein the set of images is concurrently sent to the standard radiology workflow operating in parallel with the method and automatically detecting a condition (e.g., ICH) from the set of images. Upon condition detection, the method can include any or all of, automatically: determining a second specialist from the standard radiology workflow, wherein the specialist is associated with a second point of care; notifying the second specialist on a mobile device associated with the second specialist before the radiologist notifies the first specialist; displaying a compressed version of the set of images on the mobile device; and initiating a pull of the patient (e.g., from the $1^{st}$ point of care to the $2^{nd}$ point of care, into a clinical trial protocol, from the $1^{st}$ point of care to a clinical trial at a later date, as initiated by a specialist at the $2^{nd}$ point of care, as initiated by a specialist at the $1^{st}$ point of care, as initiated by a principal investigator and/or other research coordinator of a clinical trial, etc.).

Figure 7:
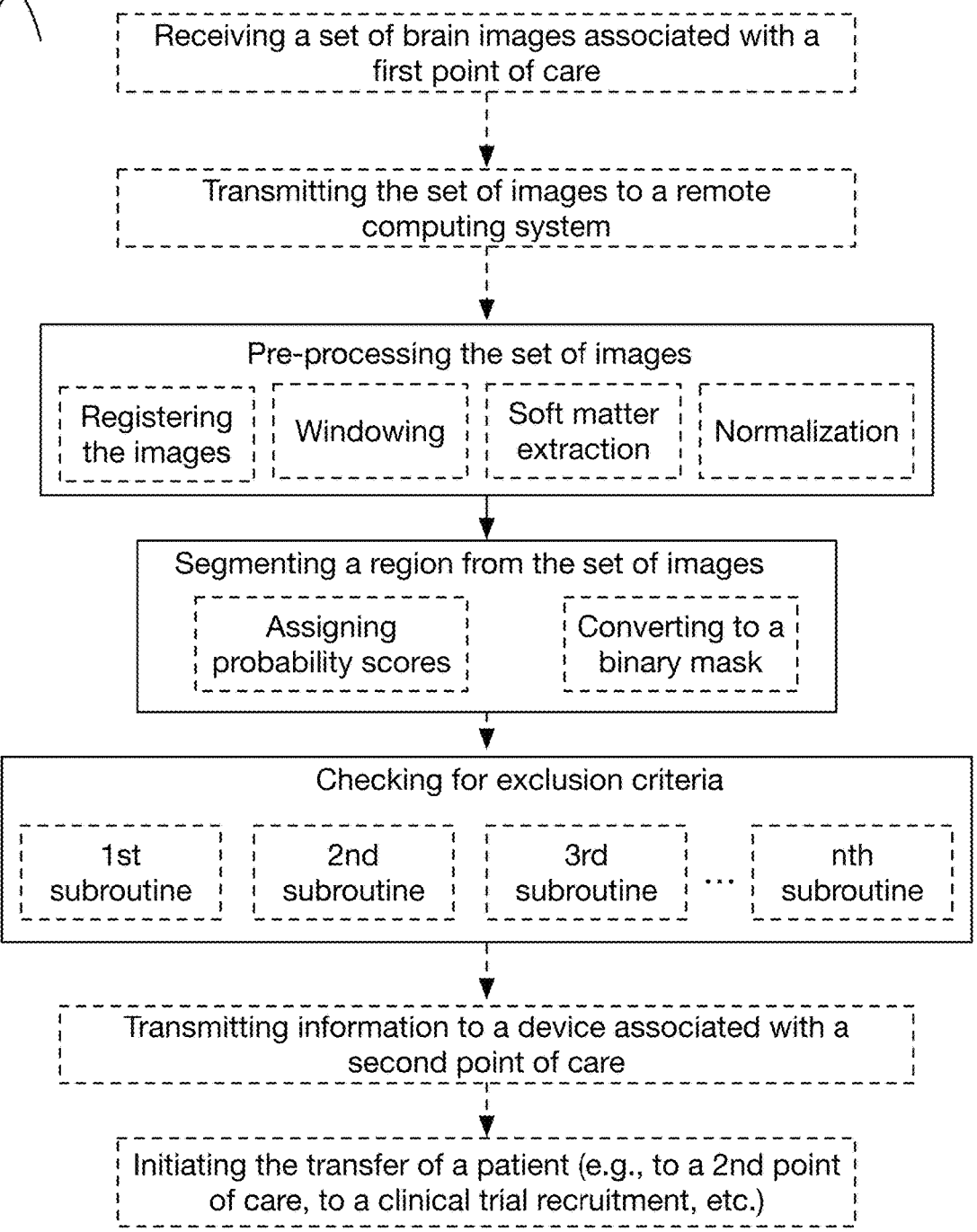
FIG. 7 depicts a variation of a method for computer-aided triage.

In a specific example (e.g., as shown in FIG. 7), the method includes, at a remote computing system, receiving a set of Digital Imaging and Communications in Medicine (DICOM) brain images associated with the patient, wherein the set of DICOM brain images is concurrently sent to a standard radiology workflow operating in parallel with the method. In the standard radiology workflow, the radiologist analyzes the set of DICOM brain images and notifies a specialist based on a visual assessment of the set of DICOM brain images at the workstation, wherein the standard radiology workflow takes a first amount of time. The method can then include detecting an ICH from the set of DICOM brain images, which includes any or all of: identifying an image dataset of a head from an NCCT scan; registering the set of images against a reference set of images, wherein an output of the registration is a straightened and resized image dataset; windowing the registered image dataset based on a predetermined range of Hounsfield units, wherein a minimum pixel value corresponds to a Hounsfield unit just below soft matter and wherein a maximum pixel value corresponds to a Hounsfield unit just above bone; assigning regions having a maximum pixel value (e.g., 255, value less than 255, etc.) to have a minimum pixel value (e.g., 0, greater than 0, etc.); normalizing the set of voxel values in the image data (e.g., to have a mean Hounsfield unit value of 24.5 HU, to have a standard deviation Hounsfield unit value of 39.5 HU, etc.); forming a 3D array containing a probability value (e.g., between 0 and 1) for each voxel in the image data, the probability value indicating a likelihood that the voxel represents a portion of an ICH; converting this probabilistic output into a binary mask defined to be all voxels having a probability score above a predetermined threshold (e.g., above 0.5, at least 0.5, between 0.3 and 1, above 0.3, less than 0.5, etc.); performing a first post-processing subroutine to assess each slice of the segmentation mask, wherein components of the segmentation mask below a size threshold (e.g., volume less than 0.4 mL) and/or less than a predetermined number of voxels away (e.g., less than 3 voxels away) from a bone voxel are eliminated from further consideration; performing a second post-processing subroutine to assess the segmentation mask (e.g., with remaining components after the $1^{st}$ subroutine, with all components from the original segmentation mask, etc.) in 3D, wherein components of the segmentation mask having a predetermined size (e.g., thickness of 1 voxel, thickness less than a predetermined threshold, etc.) are eliminated from further consideration; determining that a component of segmentation mask remains after the $1^{st}$ and $2^{nd}$ subroutines; determining that the patient has a suspected ICH; providing a notification (e.g., through texting) to a specialist associated with a $2^{nd}$ point of care (e.g., different from the $1^{st}$ point of care, within the $1^{st}$ point of care, etc.); sending a compressed image dataset to the specialist; displaying a high resolution image dataset on a workstation of the specialist; and triggering an action based on input from the specialist (e.g., transfer of patient from the $1^{st}$ point of care to the $2^{nd}$ point of care, recommending the patient for a clinical trial, etc.).

Figure 10:
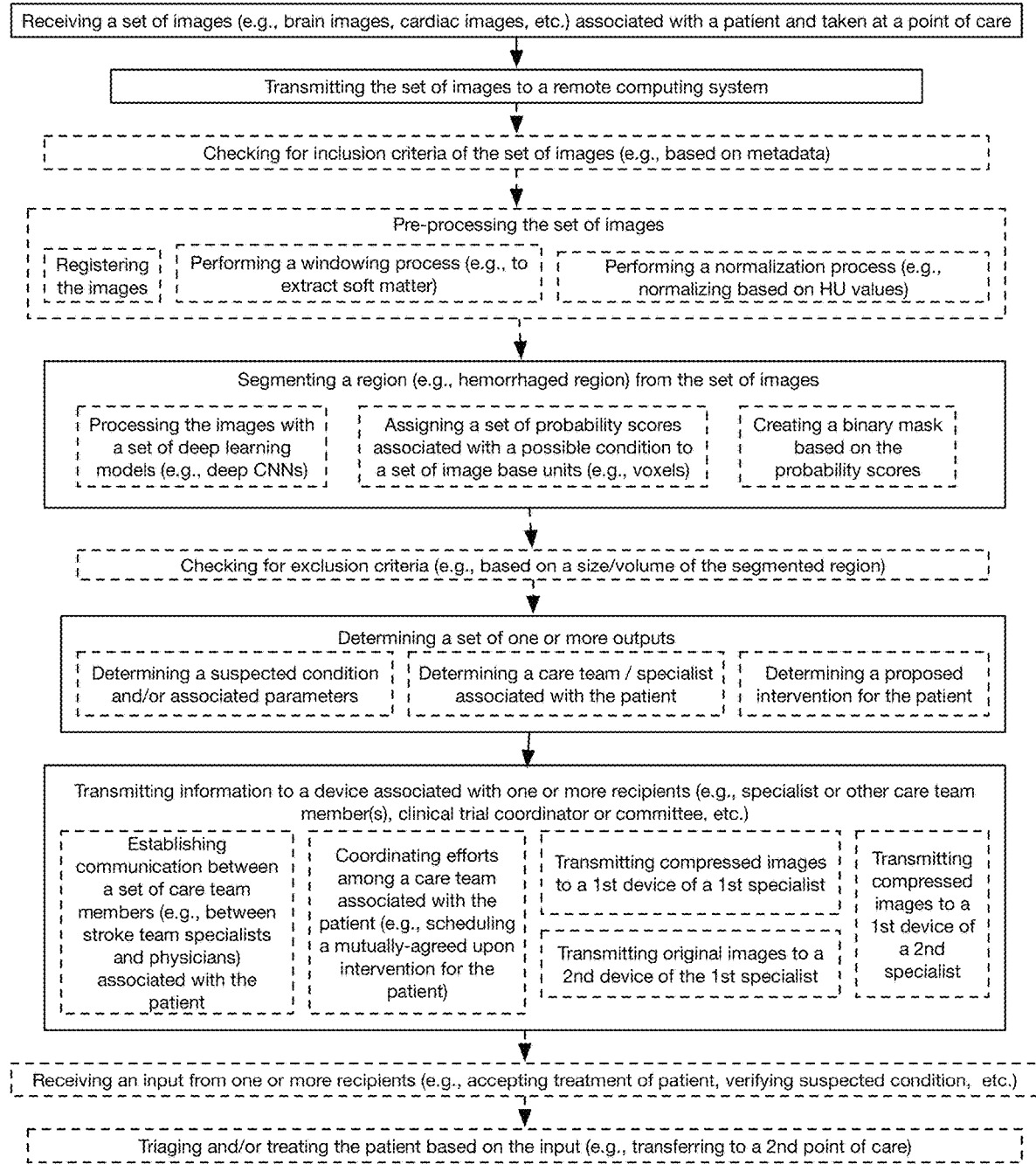
FIG. 10 depicts a variation of the method.

In a second variation of the method 200 (e.g., as shown in FIG. 10), additional or alternative to the first, the method 200 includes: receiving a set of images taken of a body region of a patient and taken a point of care; transmitting the set of images to a remote computing system; sorting and/or checking that the set of images satisfy predetermined inclusion criteria based on the metadata associated with the set of images; preprocessing the set of images, which includes a windowing process and a normalization process and optionally a registration process; segmenting a region from the set of images through a set of deep learning models, which includes assigning a set of probability scores to a set of voxels of the images and creating a binary mask based on the set of probability scores (e.g., all probability scores greater than 0.5); checking for exclusion criteria, such as a size criteria; determining a set of one or more outputs such as the determination of a suspected condition and a recipient with which to share images and notify to review the images; transmitting the notification and any suitable accompanying information to a device of the one or more recipients; receiving an input from the recipient; and triaging and/or otherwise treating the patient based on the input.

Figure 15:
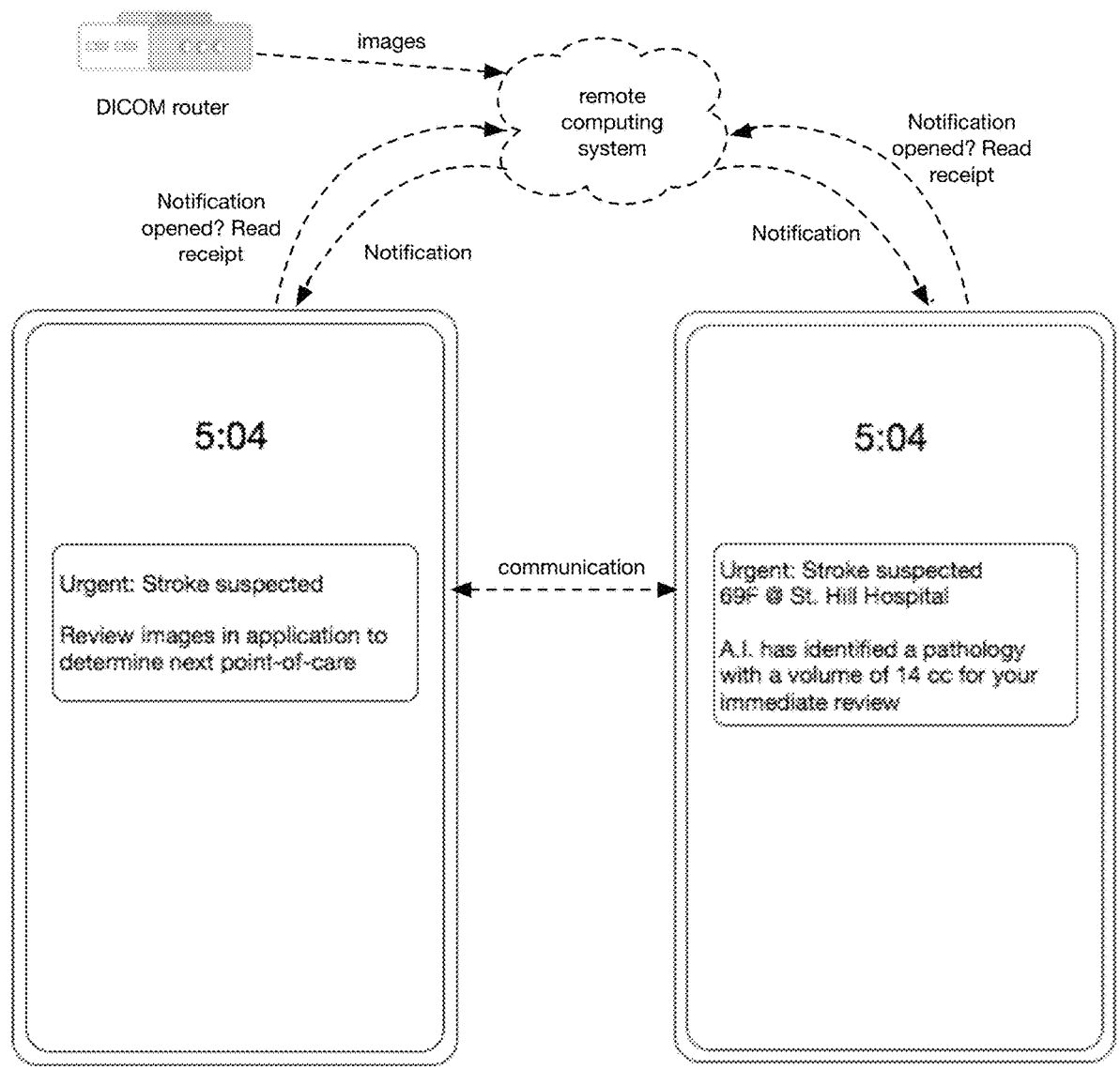
FIG. 15 depicts variations of a client application executing on a first and second user device.

In a set of specific examples, the method further includes establishing communication between users (e.g., texting, call, HIPAA-compliant texting, HIPAA-compliant calling, video call, etc.), such as between any or all of: multiple healthcare workers (e.g., physicians, surgeons, etc.), multiple research coordinators (e.g., from the same clinical trial, from different clinical trials, etc.), a healthcare worker and a research coordinator (e.g., for the research coordinator to ask questions from the surgeon, as shown in FIG. 15, etc.), a research coordinator and a patient (e.g., to submit a consent form to the patient, to receive a consent form from the patient, etc.), a healthcare worker and a patient, and/or between any other suitable users and individuals.

Figure 11:
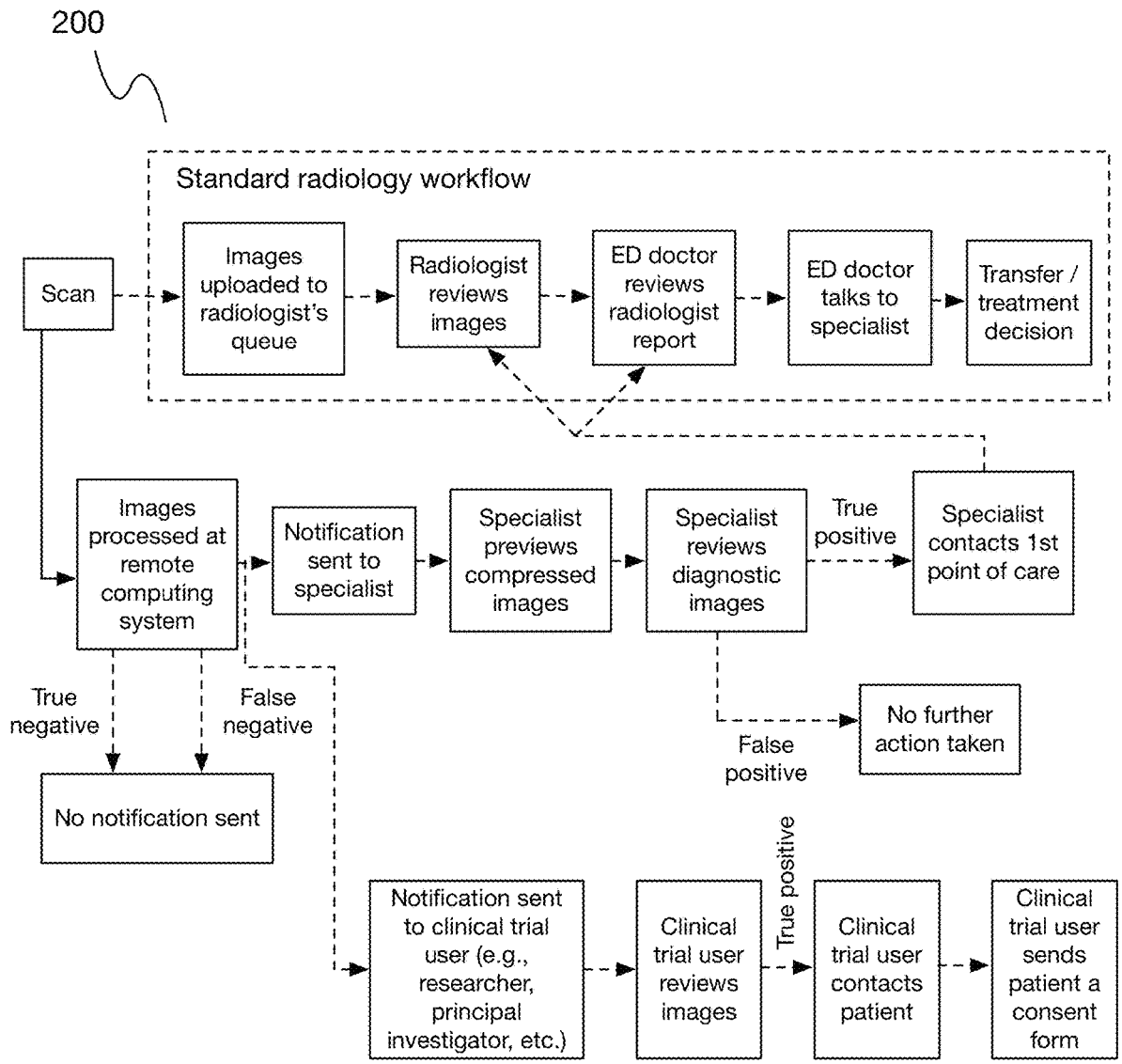
FIG. 11 depicts a variation of the method involving recommending the patient for a clinical trial.
Figure 13:
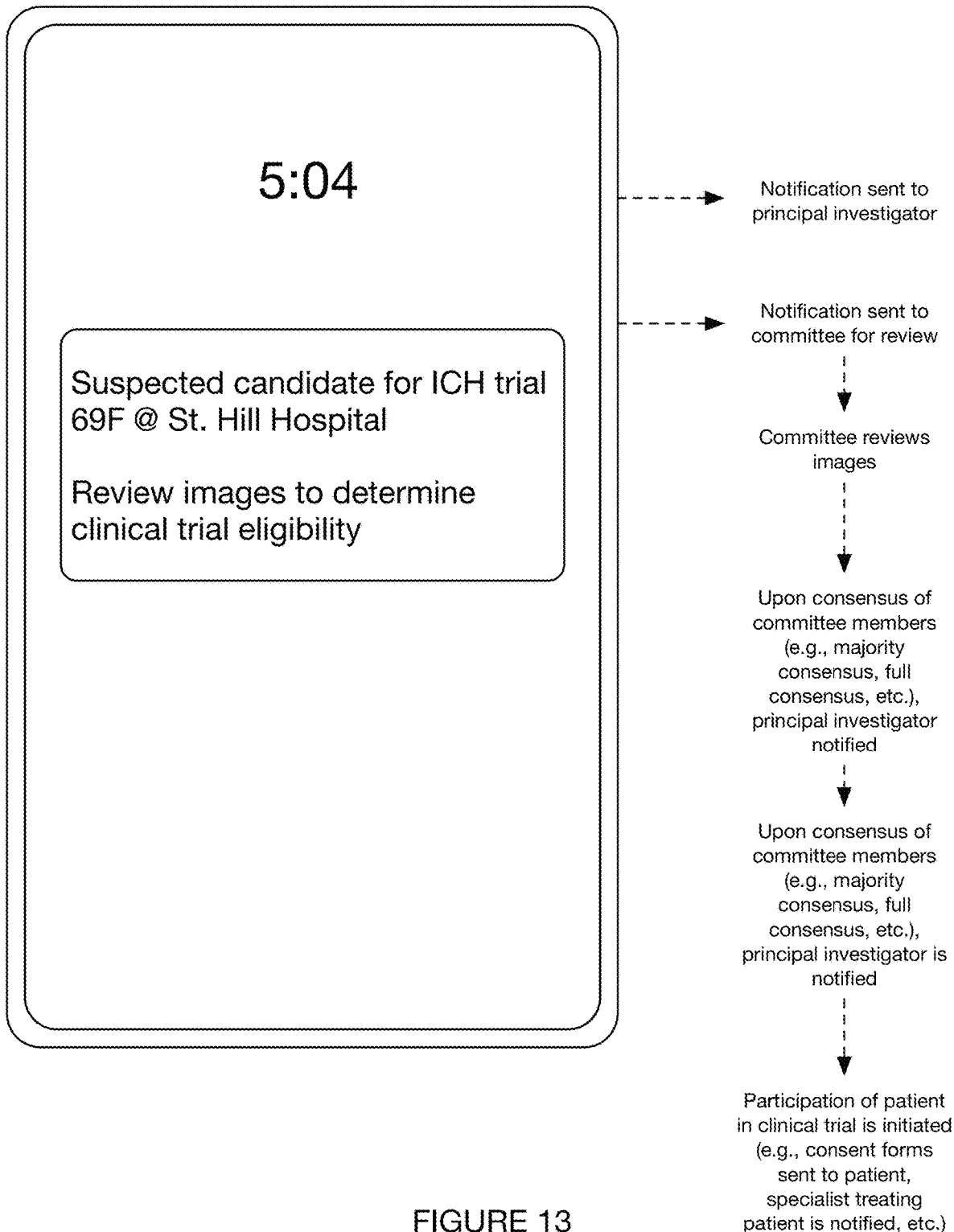
FIG. 13 depicts a variation of a notification and subsequent workflow of recommending a patient for a clinical trial.
Figure 14:
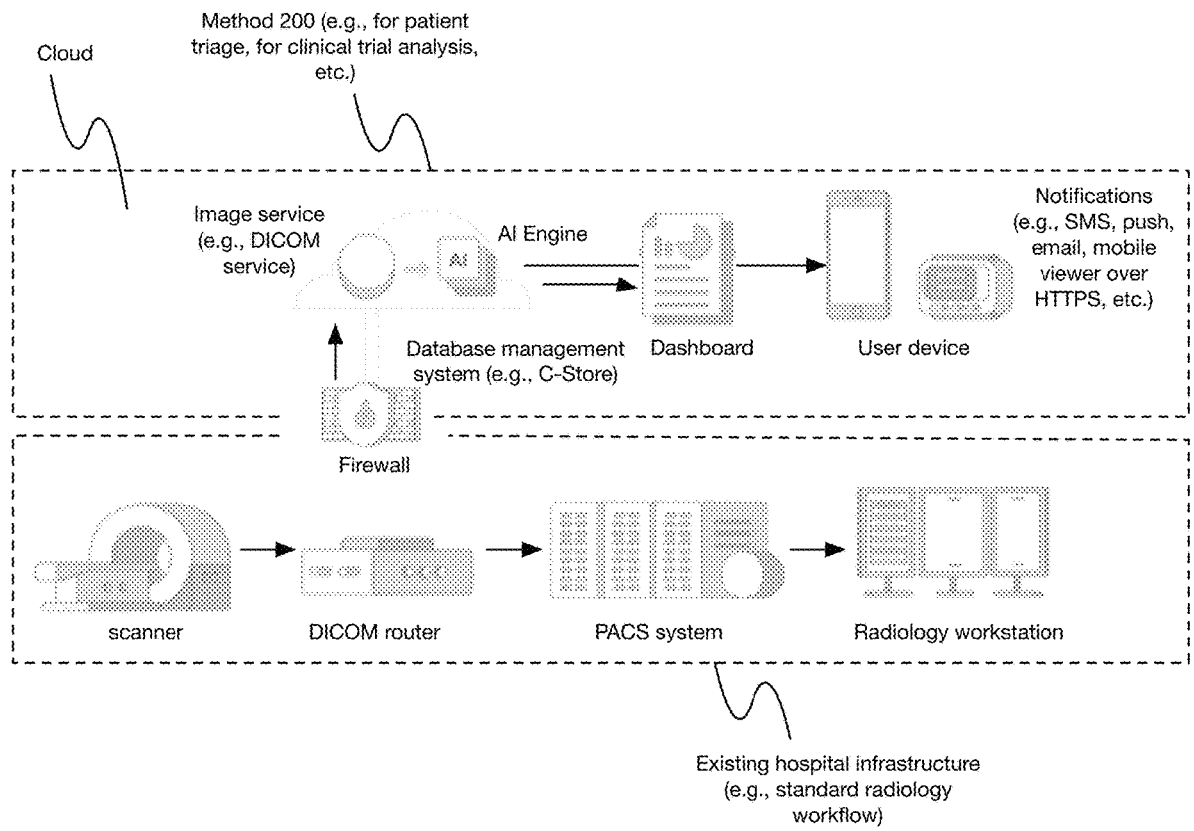
FIG. 14 depicts a variation of the system.

In a third variation of the method 200 (e.g., as shown in FIG. 11, as shown in FIG. 13, as performed in accordance with a system shown in FIG. 14, etc.), additional or alternative to those described above, the method functions to evaluate if a patient presenting with a potential pathology (e.g., stroke, ICH, LVO, etc.) qualifies for a clinical trial and if so, to alert (e.g., automatically, in a time period shorter than a determination made by a radiologist in a standard radiology workflow, etc.) a research coordinator (e.g., principal investigator) associated with the clinical trial, wherein the method includes: receiving a data packet comprising a set of images (e.g., NCCT images of a brain of the patient) sampled at the first point of care, wherein the data packet is optionally concurrently sent to the standard radiology workflow; determining an anatomical feature (e.g., large vessel region) from the set of images; determining a parameter (e.g., calculating a volume, calculating a centerline length, etc.) of the feature; comparing the parameter (e.g., centerline length) with set of clinical trial criteria (e.g., inclusion criteria, exclusion criteria, etc.); and in an event that the parameter satisfies the clinical trial criteria (e.g., according to a set of thresholds), presenting a notification on a mobile device associated with the research coordinator (e.g., as shown in FIG. 12). If the research coordinator decides to include the patient in the clinical trial (e.g., based on the notification, based on a set of compressed images sent to a user device of the research coordinator, based on a calculated parameter, based on a consensus reached by a clinical trial committee in communication with the research coordinator, etc.), the research coordinator or other user or entity can optionally transmit a consent form to the patient (e.g., to a user device of the patient, to a workstation associated with the $1^{st}$ point of care, to a workstation associated with the $2^{nd}$ point of care, etc.) and/or to a healthcare worker (e.g., to a user device of the healthcare worker, to a workstation of the healthcare worker, etc.), such as a surgeon, associated with the patient (e.g., via a client application executing on a user device of the research coordinator, from a remote computing system, etc.). Additionally or alternatively, the research coordinator can communicate (e.g., via a HIPAA-compliant messaging platform established through the client application, through a text messaging application, etc.) with a physician associated with the patient, and/or otherwise review and communicate information.

Additionally or alternatively, the method can include any or all of: providing a mobile image viewer at a client application with visible protected health information after secure login by the recipient; providing a patient status tracker to keep the recipient informed of updates to the patient; providing case volume information, which can detect and alert recipients about patients throughout the hub and spoke network that can benefit from a particular treatment (e.g., neurosurgical treatment); providing bed capacity information to a recipient, which enables increased access to early surgical intervention (e.g., thereby leading to improved patient outcomes, decreased hospital length of stay, decreased ventilator use, etc.); and/or any other processes.

Further additionally or alternatively, the method can include any other processes performed in any suitable order.

Although omitted for conciseness, the preferred embodiments include every combination and permutation of the various system components and the various method processes, wherein the method processes can be performed in any suitable order, sequentially or concurrently.

As a person skilled in the art will recognize from the previous detailed description and from the figures and claims, modifications and changes can be made to the preferred embodiments of the invention without departing from the scope of this invention defined in the following claims.

We claim:

1. A method for detecting a suspected hemorrhage, the method comprising:
   receiving a set of images associated with a patient;
   processing the set of images with a set of trained models to identify a particular region from the set of images, wherein producing the set of trained models comprises:
      performing a first training process, comprising training the set of trained models based on a first set of images labeled as positive with respect to a hemorrhage and a second set of images labeled as negative with respect to a hemorrhage;
      using the set of trained models to produce a set of outputs of the first training process;
      identifying that the set of outputs of the first training process comprises a set of false positive hemorrhage determinations; and
      updating the set of trained models by performing a second training process, comprising training the set of trained models based on the set of outputs of the first training process, the set of outputs comprising the identified set of false positive hemorrhage determinations;
   in response to detecting the suspected hemorrhage based on processing the set of images, triggering an action, the action operable to improve an efficiency of triage of the patient.

2. The method of claim 1, wherein the action is triggered at a user device associated with a specialist.

3. The method of claim 2, wherein the user device is a personal mobile user device of the specialist.

4. The method of claim 2, wherein the action triggers assignment of treatment of the patient to the specialist.

5. The method of claim 4, wherein the action comprises a notification at the user device.

6. The method of claim 1, wherein receiving the set of images, processing the set of images, and triggering the action are performed during triage of the patient.

7. The method of claim 6, wherein the patient initially arrives at a first point of care.

8. The method of claim 7, wherein the specialist is associated with a second point of care, the second point of care remote from the first point of care.

9. The method of claim 1, wherein the second training process is performed after the first training process.

10. A system for detecting a suspected hemorrhage, the system comprising:
    a set of trained models, wherein the set of trained models is produced with:
       a first training process, wherein in the first training process, the set of trained models is trained based on a first set of images labeled as positive with respect to a hemorrhage and a second set of images labeled as negative with respect to a hemorrhage;
       a false positive identification process, wherein in the false positive identification process, the set of trained models are used to produce a set of outputs of the first training process, and a set of false positive hemorrhage determinations are identified within the set of outputs of the first training process; and
       a second training process, wherein in the second training process, the set of trained models is trained based on the identified set of false positive hemorrhage determinations;
    a computing subsystem, wherein the computing subsystem:
       receives a third set of images associated with a patient; and
       processes the third set of images with the set of trained models to identify a particular region from the third set of images; and
    a client application executable on a user device of a recipient, wherein the client application:
       triggers an action in response to detecting the suspected hemorrhage based on processing the third set of images, the action operable to improve an efficiency of triage of the patient.

11. The system of claim 10, wherein the particular region comprises a segmented hyperdense region in the third set of images, wherein detecting the suspected hemorrhage comprises determining that a volume of the segmented hyperdense region exceeds a predetermined threshold.

12. The system of claim 10, wherein the set of false positive hemorrhage determinations is produced as a set of outputs of the first training process.

13. The system of claim 10, wherein the second training process is performed after the first training process.

14. A method for detecting a suspected hemorrhage, the method comprising:
    training a set of models to produce a trained set of models, comprising training the set of models based on:
       a first set of images having a first set of labels, the first set of labels indicating a presence of a hemorrhage;
       a second set of images having a second set of labels, the second set of labels indicating an absence of a hemorrhage; and
       a third set of images having a third set of labels, the third set of labels indicating a false positive detection of a hemorrhage by a trained model;
    receiving a fourth set of images associated with a patient;
    processing the fourth set of images with the trained set of models; and
    triggering an action in response detecting the suspected hemorrhage based on processing the fourth set of images, the action operable to improve an efficiency of triage of the patient.

15. The method of claim 14, wherein the fourth set of images is imaged at a first point of care, and wherein the action comprises an initiation of a transfer of the patient to a second point of care, the second point of care remote from the first point of care.

16. The method of claim 15, wherein the action is triggered automatically.

17. The method of claim 14, wherein the action triggers transmission of a notification to a specialist located at a $2^{nd}$ point of care remote from a $1^{st}$ point of care at which the patient is located, wherein an input from the specialist in response to the notification triggers an assignment of treatment of the patient to the specialist.

18. The method of claim 14, wherein the third set of images is a subset of the first set of images, and wherein the third set of labels replaces the first set of labels originally determined for the subset of the first set of images.

19. The method of claim 18, wherein training the set of models comprises a first training process, wherein in the first training process, the set of models is trained based on the first and second sets of images, wherein in the second training process, the set of models is trained based on the third set of images, and wherein the second training process is performed after the first training process.

20. The method of claim 14, wherein processing the fourth set of images comprises determining a severity score associated with the suspected hemorrhage, wherein the action is determined at least in part based on the severity score.

21. The method of claim 1, further comprising, prior to processing the set of images, evaluating one or more exclusion criteria based on the set of images, comprising eliminating one or more categories of false positives associated with hemorrhage determinations based on the set of images.

* * * * *

UNITED STATES PATENT AND TRADEMARK OFFICE
CERTIFICATE OF CORRECTION

PATENT NO. : 12,068,070 B2
APPLICATION NO. : 17/895778
DATED : August 20, 2024
INVENTOR(S) : Christopher Mansi et al.

It is certified that error appears in the above-identified patent and that said Letters Patent is hereby corrected as shown below:

In the Claims

Column 36, Line 49, In Claim 14, after "response", insert --to--

Signed and Sealed this
First Day of October, 2024

Katherine Kelly Vidal
*Director of the United States Patent and Trademark Office*